US009126136B2

(12) United States Patent
Ye et al.

(10) Patent No.: US 9,126,136 B2
(45) Date of Patent: Sep. 8, 2015

(54) REVERSIBLE CURRENT GEL ELECTROPHORESIS DEVICE FOR SEPARATING BIOLOGICAL MACROMOLECULES

(71) Applicants: Zheng Ye, Portland, OR (US); William D. Mathers, Lake Oswego, OR (US); Ed Brightman, Portland, OR (US)

(72) Inventors: Zheng Ye, Portland, OR (US); William D. Mathers, Lake Oswego, OR (US); Ed Brightman, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 13/928,200

(22) Filed: Jun. 26, 2013

(65) Prior Publication Data

US 2013/0284599 A1    Oct. 31, 2013

Related U.S. Application Data

(63) Continuation of application No. 13/393,529, filed as application No. PCT/US2010/047563 on Sep. 1, 2010, now Pat. No. 8,496,798.

(60) Provisional application No. 61/239,017, filed on Sep. 1, 2009.

(51) Int. Cl.
*B01D 57/02* (2006.01)
*G01N 27/447* (2006.01)
*G01N 33/68* (2006.01)

(52) U.S. Cl.
CPC .......... *B01D 57/02* (2013.01); *G01N 27/44756* (2013.01); *G01N 27/44773* (2013.01); *G01N 33/6803* (2013.01)

(58) Field of Classification Search
CPC .................. G01N 27/44756; G01N 27/44773; G01N 33/6803; B01D 57/02
USPC .................................. 204/600–621, 450–470
See application file for complete search history.

(56) References Cited

U.S. PATENT DOCUMENTS

| 4,699,706 A | 10/1987 | Burd et al. |
| 4,964,961 A | 10/1990 | Brautigam et al. |

(Continued)

FOREIGN PATENT DOCUMENTS

| JP | 63-222254 | 9/1988 |
| JP | 07-322899 | 12/1995 |

(Continued)

OTHER PUBLICATIONS

Abramovitz et al., "Recovery of native proteins from preparative electrophoresis gel slices by reverse polarity elution," *Preparative Biochemistry*, 14(3), 205-221, (1984).

(Continued)

*Primary Examiner* — J. Christopher Ball
(74) *Attorney, Agent, or Firm* — Klarquist Sparkman, LLP

(57) ABSTRACT

Cassette bodies for use with electrophoresis apparatus can be formed of a single piece of molded or machined plastic. Such cassette bodies can include a plurality of channels that pass through the cassette body, from a proximal end to a distal end. Such channels can be defined by upper and lower chambers. The upper chambers can be in fluid communication with a first buffer pool through a semi-permeable membrane, and the lower chambers can be in fluid communication with a second buffer pool. An electric current can be passed through the first and second buffer pools, and then reversed, to perform an electrophoresis operation that can separate a biomolecule of interest from free probes, and provide for convenient collection of said biomolecule of interest.

9 Claims, 9 Drawing Sheets

(56) References Cited

U.S. PATENT DOCUMENTS

| | | |
|---|---|---|
| 5,041,203 A | 8/1991 | Serwer |
| 5,137,609 A | 8/1992 | Manian et al. |
| 5,176,805 A | 1/1993 | Tombs |
| 5,221,454 A | 6/1993 | Manian et al. |
| 5,340,449 A | 8/1994 | Shukla |
| 5,427,664 A | 6/1995 | Stoev et al. |
| 5,538,614 A | 7/1996 | Han |
| 5,560,811 A | 10/1996 | Briggs et al. |
| 5,562,813 A | 10/1996 | Mullaart et al. |
| 5,571,680 A | 11/1996 | Chen |
| 5,650,055 A | 7/1997 | Margolis |
| 5,773,645 A | 6/1998 | Hochstrasser |
| 5,853,668 A | 12/1998 | Begg et al. |
| 6,027,628 A | 2/2000 | Yamamura et al. |
| 6,103,537 A | 8/2000 | Ullman et al. |
| 6,129,828 A | 10/2000 | Sheldon, III et al. |
| 6,146,511 A | 11/2000 | Slater et al. |
| 6,398,933 B1 | 6/2002 | Scott |
| 7,179,658 B2 | 2/2007 | Cheng et al. |
| 7,365,847 B2 | 4/2008 | Auton et al. |
| 2005/0155861 A1 | 7/2005 | Guzman |
| 2007/0284250 A1 | 12/2007 | Magnant et al. |
| 2008/0047835 A1 | 2/2008 | MacConnell |
| 2009/0071832 A1 | 3/2009 | Xie et al. |

FOREIGN PATENT DOCUMENTS

| | | |
|---|---|---|
| WO | WO 93/15392 | 8/1993 |
| WO | WO 99/18438 A | 4/1999 |
| WO | WO 03/010528 | 2/2003 |

OTHER PUBLICATIONS

Hellman and Fried, "Electrophoretic shift assay (EMSA) for detecting protein-nucleic acid interactions," Nat. Protoc., 2(8), 1849-1861, (2007).

International Search Report and Written Opinion mailed Nov. 9, 2009; issued in corresponding International PCT Application No. PCT/US2009/035689, filed Feb. 3, 2009.

International Search Report and Written Opinion, dated Mar. 17, 2011, issued by the Korean Intellectual Property Office in related International Patent Application No. PCT/US2010/047563, 13 pp.

Lee et al., "Reversible Capture of Genomic DNA by a Nafion-coated Electrode," *Analytical Biochemistry*, 380:335-337 (2008).

Supplementary European Search Report issued Feb. 10, 2014, by the European Patent Office for EP 10814443.7, 8 pp.

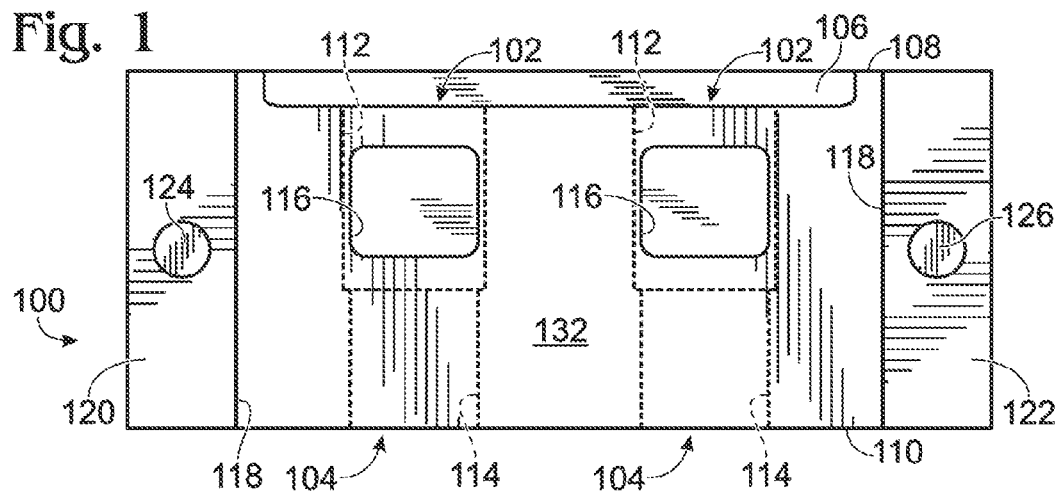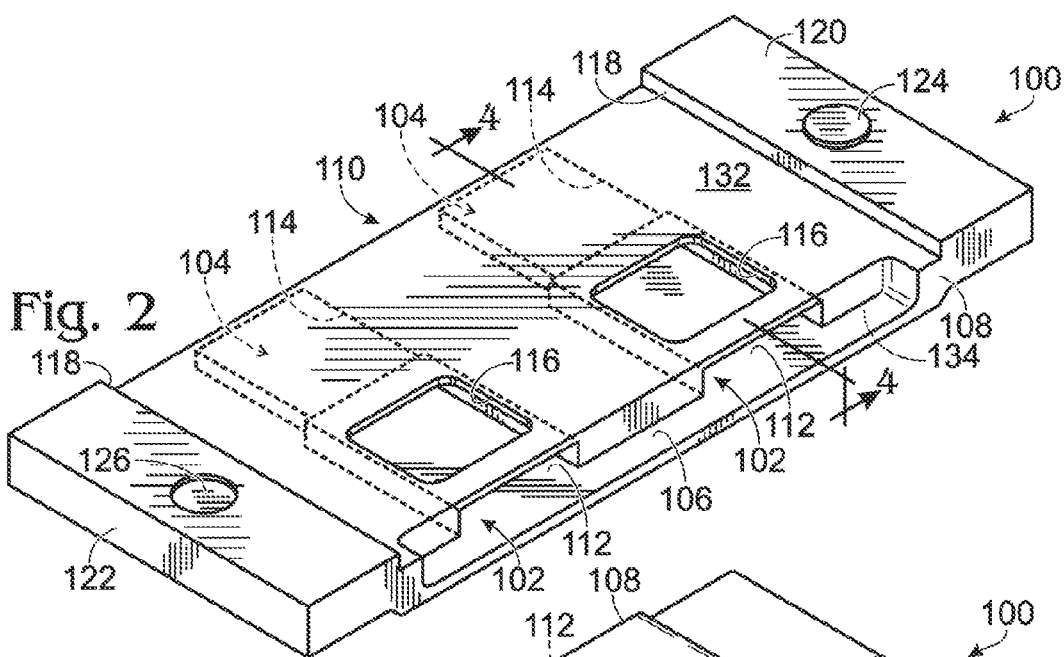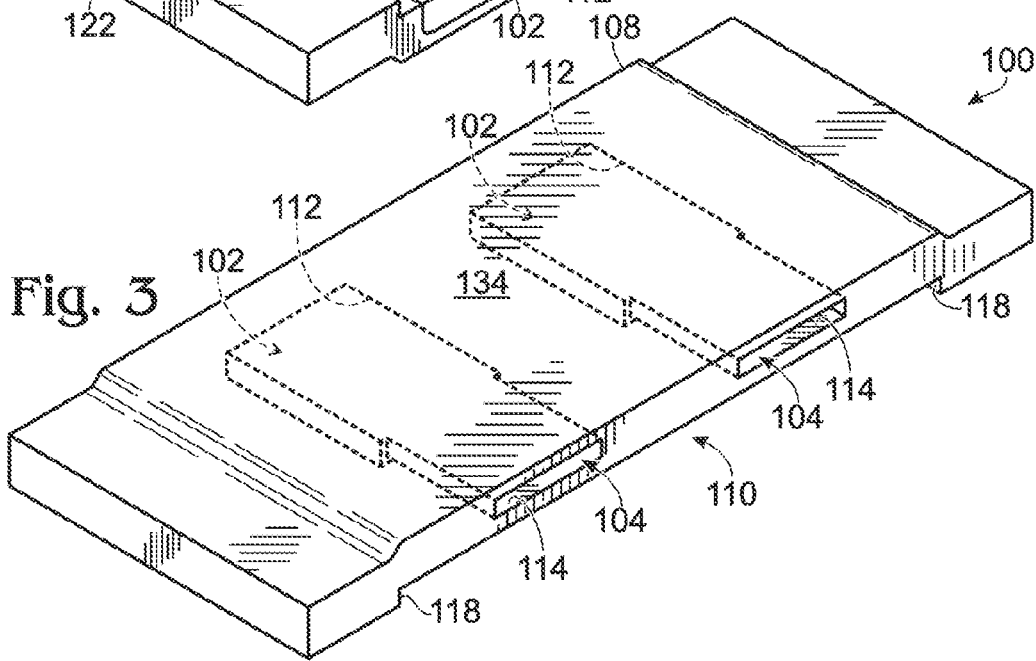

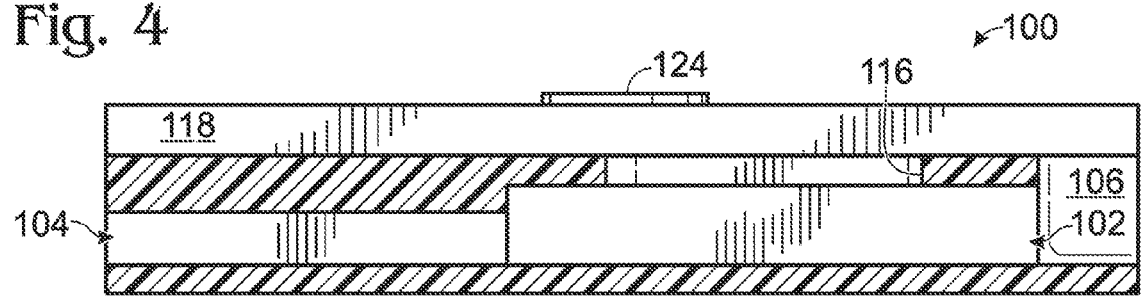
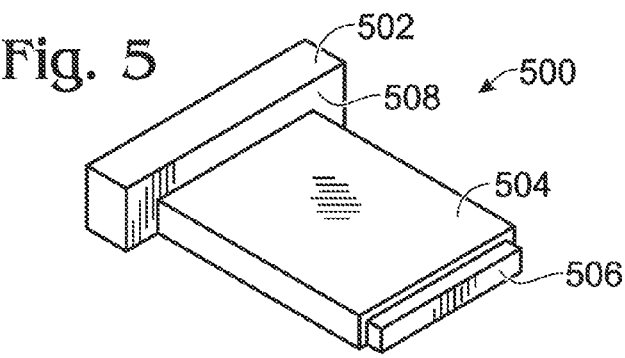
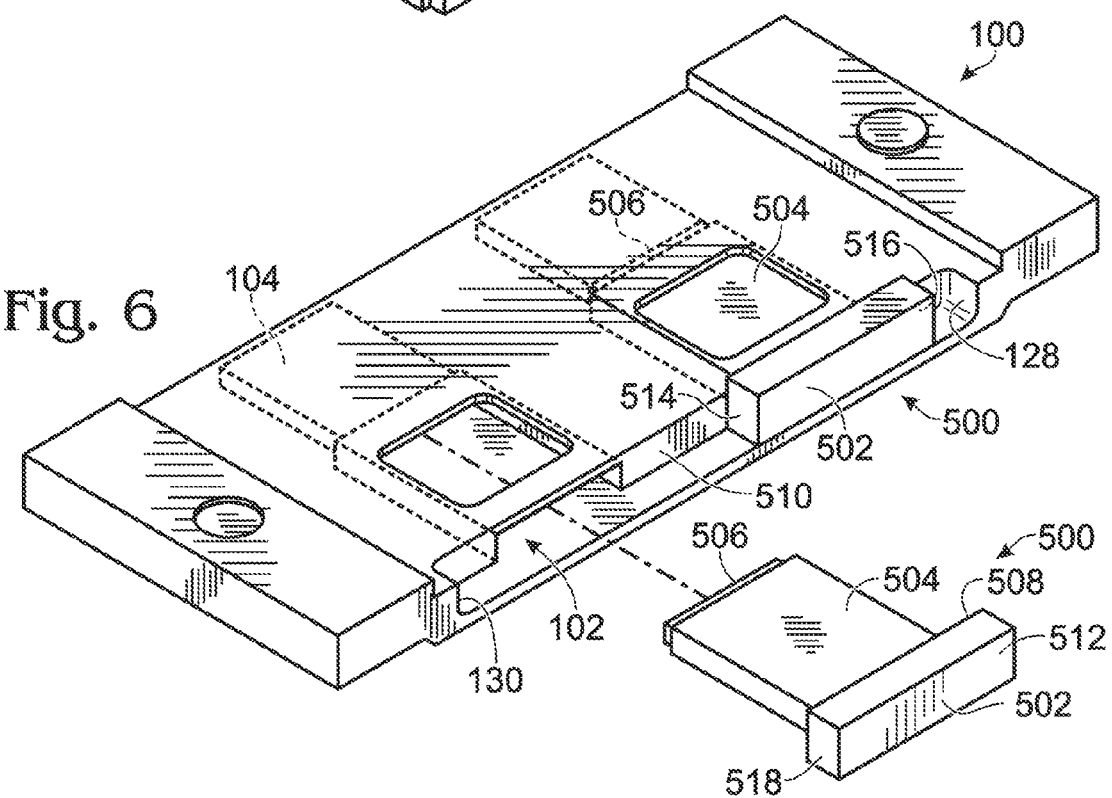

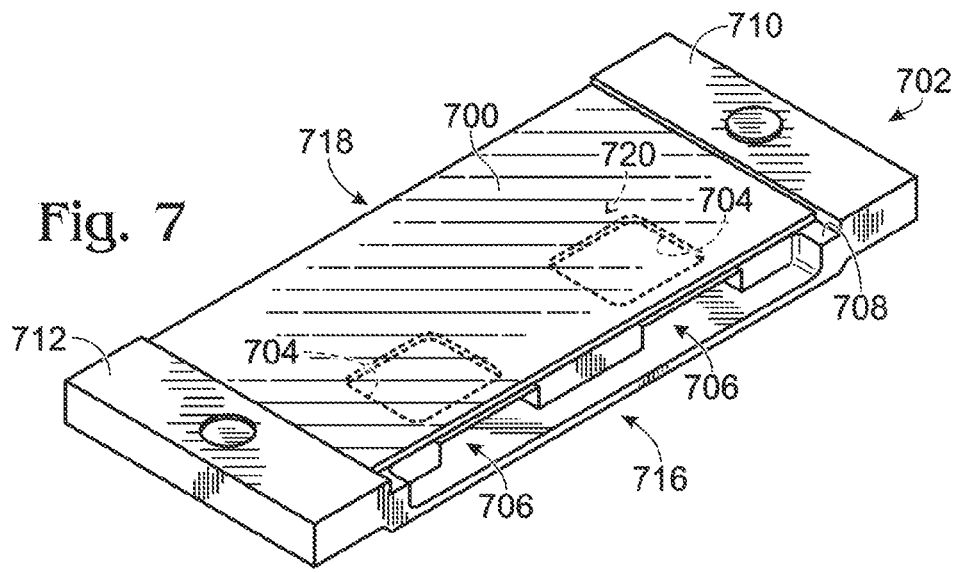
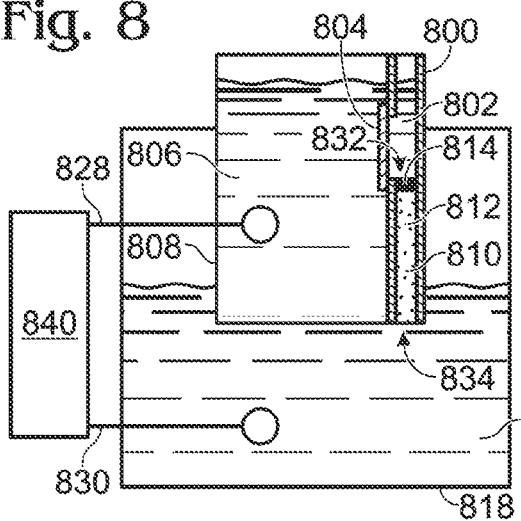 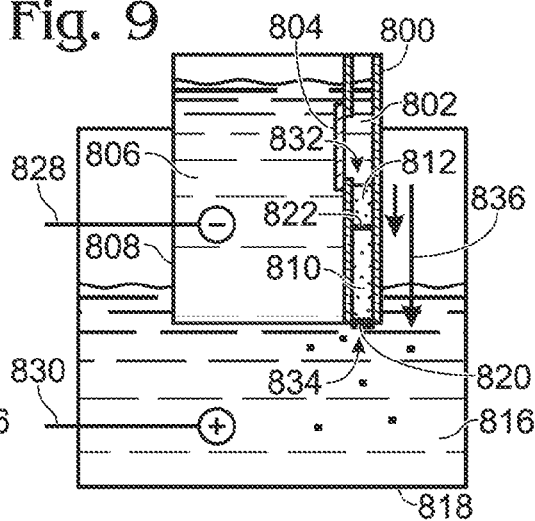
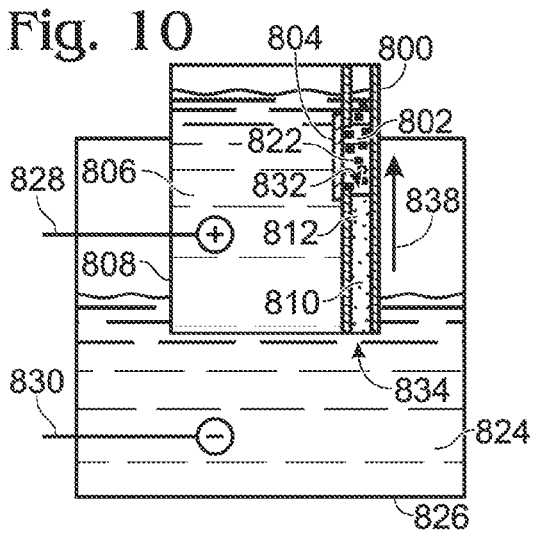

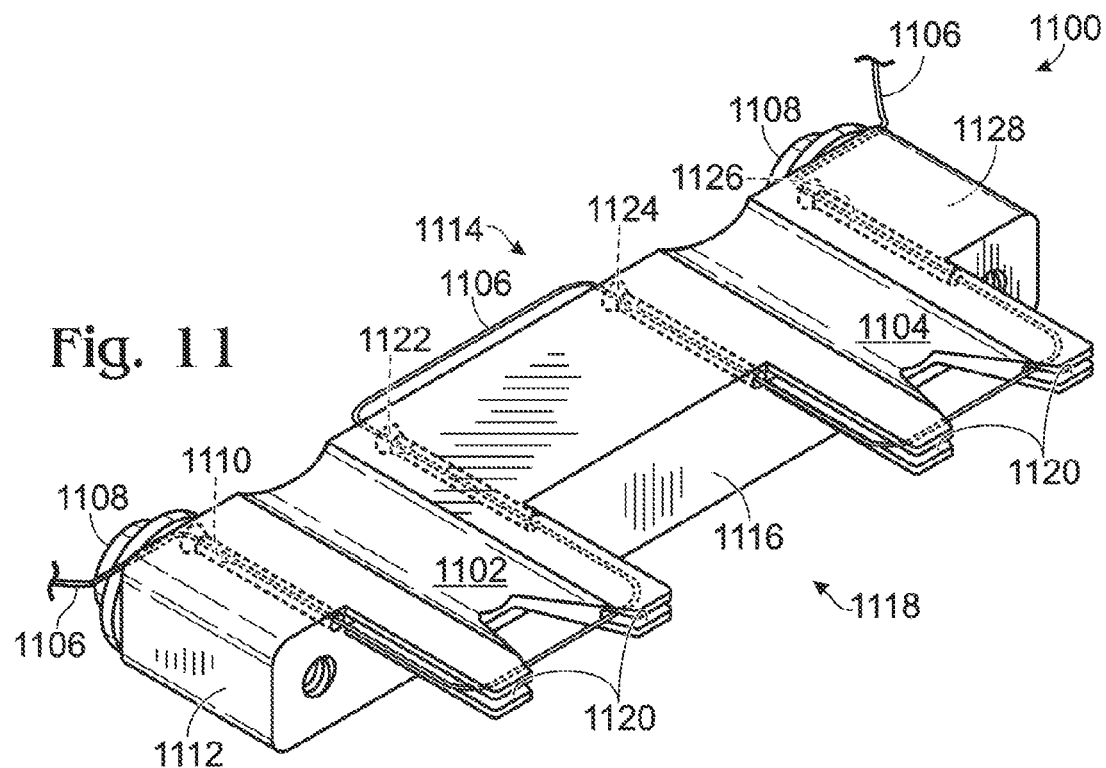
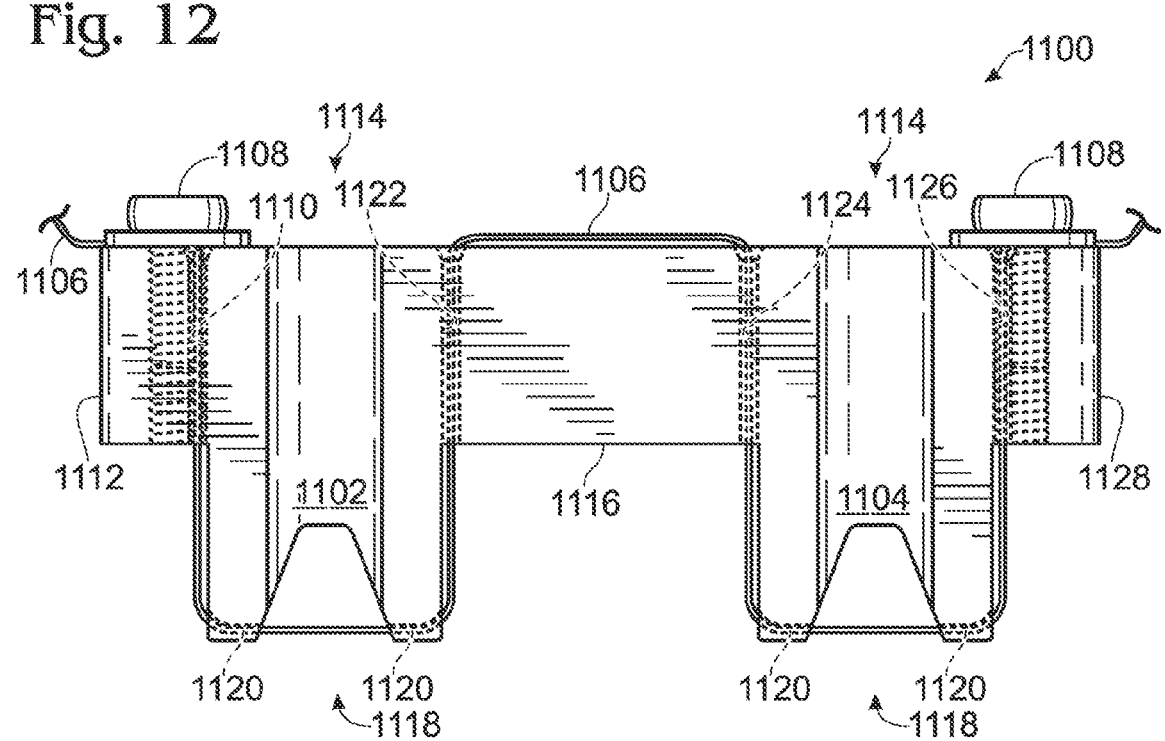

REVERSIBLE CURRENT GEL ELECTROPHORESIS DEVICE FOR SEPARATING BIOLOGICAL MACROMOLECULES

CROSS REFERENCE TO RELATED APPLICATIONS

This is a continuation of U.S. patent application Ser. No. 13/393,529, filed Feb. 29, 2012, which is the U.S. National Stage of International Application No. PCT/US2010/047563, filed Sep. 1, 2010, which was published in English under PCT Article 21(2), which in turn claims the benefit of U.S. Provisional Patent Application No. 61/239,017, entitled "Reversible Current Gel Electrophoresis Device for Separating Biological Macromolecules," filed Sep. 1, 2009, the disclosure of which is incorporated herein by reference in its entirety.

FIELD

This disclosure concerns a device for the electrophoretic purification of biological macromolecules and methods of using such devices.

BACKGROUND

Electrophoresis is a method used to separate and analyze biological macromolecules, including proteins, DNA, RNA, and complexes of these molecules. Numerous electrophoretic techniques have been developed including capillary electrophoresis, gel electrophoresis, paper electrophoresis, and immunoelectrophoresis.

A common electrophoretic method is gel electrophoresis. In gel electrophoresis, a gel is formed using compounds such as agarose or polyacrylamide. A mixture containing the desired compound(s) is placed (or loaded) onto one end of the gel, and the gel is then placed contact with a liquid buffer. This liquid buffer contains salts, which, when dissolved, form ions within the buffer.

Biological molecules are typically charged, for example when contacted with electrophoresis buffer. For example, DNA is negatively charged in common electrophoresis buffers due to the phosphate groups in its backbone. Therefore, when electric current is applied to the ends of the gel, the biological molecules move through the gel from one end to the other. Depending on their size, shape, and charge, some molecules move through the gel faster than others. As the mixture moves through the gel, molecules of one size, shape, or charge are separated from those of a different size, shape, and/or charge. The speed at which the molecules pass through the gel and the separation between the various types of molecules also depends on the concentration and type of the gel. In general, molecules pass through thicker gels slower than they do through thinner gels, though thicker gels typically provide better separation.

The gels can be run horizontally and/or vertically. When run horizontally, the gel is generally submerged in the buffer. The sample mixture is loaded at one end and run to the other end. When the gel is run vertically, the sample mixture is loaded at the top of the gel and run towards the bottom. A vertical gel is generally not submerged in buffer. Rather it is run on an electrophoresis apparatus that contains a buffer chamber at the top and the bottom of the gel.

Conventional electrophoresis apparatus include cassettes that are typically two parallel glass plates held apart by spacers. Separation of biomolecules within an electrophoresis gel is easily achieved; however, subsequent collection of the isolated molecules for further analysis can be inefficient and difficult. This is especially true when the individual biomolecules or complexes containing the biomolecules have different physical characteristics, such as molecular weights and/or charges. For example, in traditional gel electrophoresis, as a mixture of biomolecules moves through the gel, molecules of one size, shape, or charge are separated from those of a different size, shape, and/or charge. Thus, biomolecules of interest can be spread apart within the cross-linked gel, leaving them not easily accessible. There thus remains a need for improved electrophoresis apparatus that addresses these and other issues.

SUMMARY

To overcome the problems with conventional gel electrophoretic separation and purification devices, devices for separating biomolecules of interest in a complex from free biomolecules and methods of using those devices are disclosed herein. While the devices are described with reference to the separation of complexes of biomolecules of interest, it will be appreciated by those of ordinary skill in the art that any group of large molecules can be separated from a set of smaller molecules by the disclosed methods and devices.

One embodiment of a cassette for use with an electrophoresis device comprises a proximal end and a distal end opposite the proximal end, a front face and a back face substantially parallel to the front face, and at least one chamber defined between the front face and the back face, the chamber having an upper portion and a lower portion, wherein the upper portion includes an upper opening at or near the proximal end of the cassette and the lower portion includes a lower opening at or near the distal end of the cassette, and wherein the front face comprises at least one window opening into the upper portion of the chamber.

In some embodiments, the cassette can further comprise a semi-permeable membrane covering at least a portion of the at least one window opening. The semi-permeable membrane can be removably secured to the front face of the cassette. The semi-permeable membrane can be configured to allow passage of a buffer solution surrounding at least a portion of the cassette, and to at least partially block passage of a biomolecule contained within the upper portion of the at least one chamber. In some embodiments, a semi-permeable membrane can substantially block passage of a biomolecule of interest, thus substantially preventing it from exiting the chamber through the window opening.

Some embodiments of a cassette according to the present disclosure comprise acrylic. Some embodiments of a cassette comprise a unitary body. Cassettes according to the present disclosure can be integrated with one or more other components to form an electrophoresis device.

One embodiment of an electrophoresis device comprises a cassette, wherein the cassette comprises a proximal end and a distal end opposite the proximal end, a front face and a back face substantially parallel to the front face, and at least one chamber defined between the front face and the back face, the chamber having an upper portion and a lower portion, wherein the upper portion includes an upper opening at or near the proximal end of the cassette and the lower portion includes a lower opening at or near the distal end of the cassette, and wherein the front face comprises at least one window opening into the upper portion of the chamber. The electrophoresis device can further comprise a first buffer solution in fluid contact with the lower opening of the lower portion, a second buffer solution in fluid contact with the window opening of the upper portion, and at least one electrode electrically coupled to each of the first and second buffer solutions. Fluid contact can include both direct and indirect fluid contact. For example, fluid contact can include fluid contact through a membrane, such as a semi-permeable membrane.

In some embodiments of an electrophoresis device, the cassette further comprises a semi-permeable membrane covering at least a portion of the window opening of the upper portion, such as a membrane comprising cellulose or cellophane.

Disclosed devices can be used to perform reversible current electrophoresis, such that when current is run in a first direction, free molecules elute into the buffer at the distal end of the device. Then the cassette body can be placed into a new bath, the current reversed, and the biomolecules of interest can then move in the opposite direction, out of the gel, and back into the buffer solution at the proximal end of the cassette body, where they can then be easily collected from the device.

For example, one method of separating a biomolecule of interest from a sample comprises providing a sample, wherein the sample contains a biomolecule of interest and free probes, loading the sample onto a gel in a lower portion of a cassette body, electrophoresing the sample by applying a current for a time period sufficient for substantially all of the free probes to elute out of a distal end of the lower portion, into a first buffer solution in a first buffer container, leaving the biomolecule of interest within the gel, removing the first buffer solution, providing a new buffer solution in fluid contact with the lower portion of the cassette, reversing the current with respect to the gel, and electrophoresing the sample for a time period sufficient for substantially all of the biomolecule of interest to elute out of a proximal end of the lower portion, into an upper portion of the cassette body.

Disclosed methods can further comprise collecting biomolecule of interest. Collecting the biomolecule of interest can comprise withdrawing a volume of buffer solution containing the biomolecule of interest from the upper portion of the cassette body. Collecting the biomolecule of interest can comprise securing a semi-permeable membrane over at least part of the upper portion, so as to prevent substantially all of the biomolecule of interest from passing through the semipermeable membrane into a second buffer solution in fluid contact with the upper portion of the cassette.

In some methods, reversing the current with respect to the gel comprises switching the polarity of a first and second electrode in electrical contact with the first and second buffer solutions, respectively. In some methods, reversing the current with respect to the gel comprises changing the orientation of the gel with respect to a first and second electrode in electrical contact with the first and second buffer solutions, respectively.

Removing the first buffer solution can comprise draining the first buffer solution from a buffer container. Providing a new buffer solution in fluid contact with the lower portion of the cassette can comprise refilling the buffer container with the new buffer solution. In other methods, removing the first buffer solution comprises removing the cassette from a first buffer container containing the first buffer solution, and providing a new buffer solution in fluid contact with the lower portion of the cassette comprises placing the cassette in a second buffer container containing the new buffer solution.

The foregoing and other objects, features, and advantages of the invention will become more apparent from the following detailed description, which proceeds with reference to the accompanying figures.

BRIEF DESCRIPTION OF THE DRAWINGS

FIG. 1 is a front elevation view of one embodiment of an electrophoresis cassette body according to the present disclosure.

FIG. 2 is a perspective view of one embodiment of an electrophoresis cassette body.

FIG. 3 is an alternate perspective view of one embodiment of an electrophoresis cassette body.

FIG. 4 is a cross sectional view taken across line 4-4 in FIG. 2.

FIG. 5 is a perspective view of one embodiment of a comb that can be used with cassette bodies of the present disclosure.

FIG. 6 is a perspective view showing the placement of combs into a cassette body.

FIG. 7 is a perspective view of a cassette body having a membrane, according to one embodiment of the present disclosure.

FIG. 8 is a schematic cross sectional view of a cassette body in place within a buffer bath.

FIG. 9 is a schematic cross sectional view of the cassette body and buffer bath of FIG. 8, after current has been applied.

FIG. 10 is a schematic cross sectional view of the cassette body of FIGS. 8-9, in place in a new buffer bath.

FIG. 11 is a perspective view of an electrode insert.

FIG. 12 is a front elevation view of one embodiment of an electrode insert.

DETAILED DESCRIPTION

I. Terms

Figure 13:
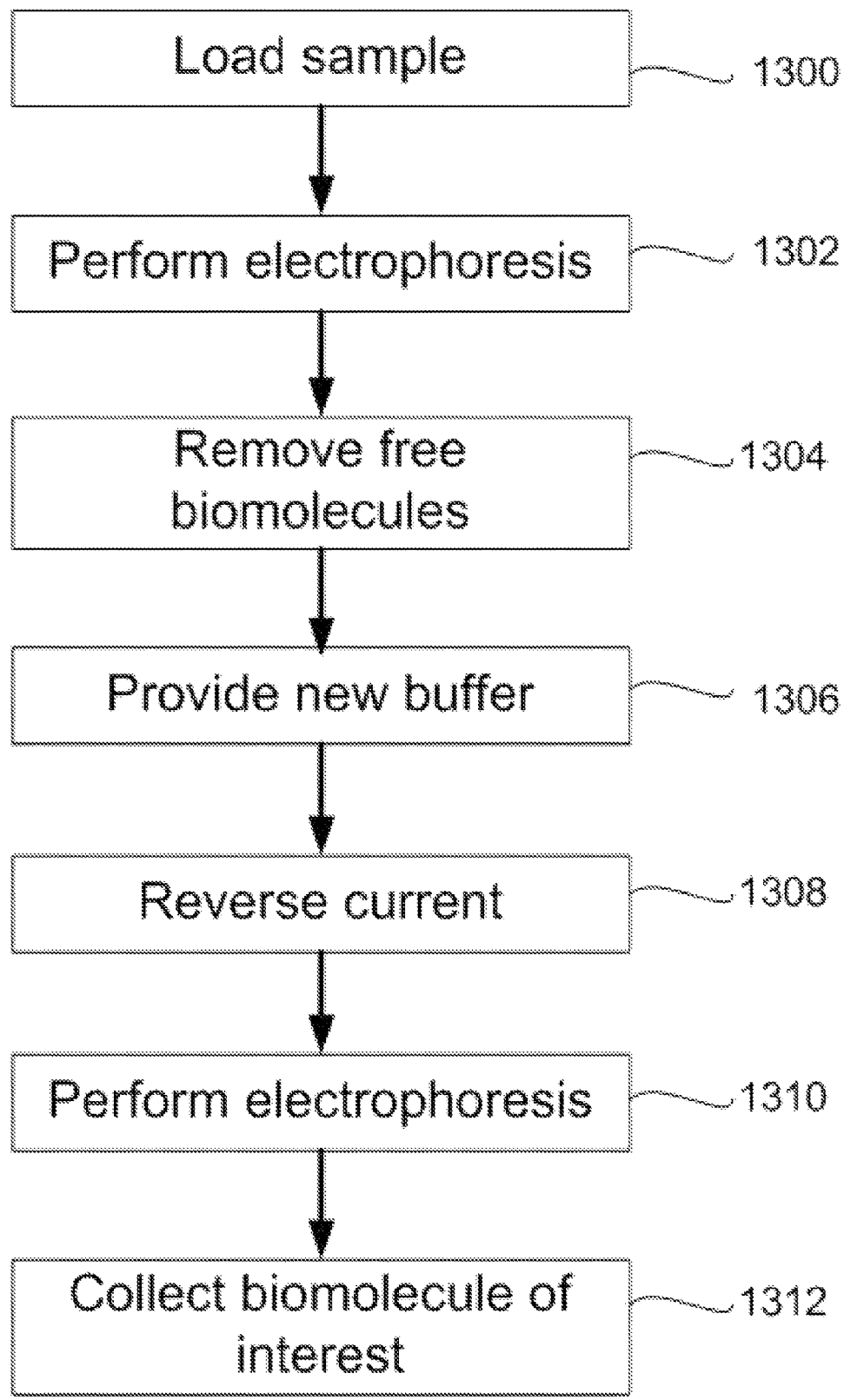
FIG. 13 is a block diagram of one method of performing an electrophoresis gel.

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proleomics,* 2nd Edition, 2003 (ISBN: 0-471-26821-6).

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a probe" includes single or plural probes and is considered equivalent to the phrase "comprising at least one probe." The term "or"

refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Although methods and materials similar or equivalent to those described herein can be used in the practice or testing of the present disclosure, suitable methods and materials are described below. The materials, methods, and examples are illustrative only and not intended to be limiting.

To facilitate review of the various embodiments of this disclosure, the following explanations of specific terms are provided:

Antibody: A polypeptide ligand that includes at least a light chain or heavy chain immunoglobulin variable region and specifically binds an epitope of an antigen. Antibodies can include monoclonal antibodies, polyclonal antibodies, or fragments of antibodies.

The term "specifically binds" refers to, with respect to an antigen, the preferential association of an antibody or other ligand, in whole or part, with a specific polypeptide, such as a specific double-stranded DNA binding protein, for example a transcription factor, such as an activated transcription factor. A specific binding agent binds substantially only to a defined target. It is recognized that a minor degree of non-specific interaction may occur between a molecule, such as a specific binding agent, and a non-target polypeptide. Nevertheless, specific binding can be distinguished as mediated through specific recognition of the antigen. Although selectively reactive antibodies bind antigen, they can do so with low affinity. Specific binding typically results in greater than 2-fold, such as greater than 5-fold, greater than 10-fold, or greater than 100-fold increase in amount of bound antibody or other ligand (per unit time) to a target polypeptide, such as compared to a non-target polypeptide. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, *A Laboratory Manual*, Cold Spring Harbor Publications, New York (1988), for a description of immunoassay formats and conditions that can be used to determine specific immunoreactivity.

Antibodies can include a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, Immunology, 3rd Ed., W.H. Freeman & Co., New York, 1997.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Aptamer: Small nucleic acid or peptide molecules that bind a specific target molecule, such as a target biomolecule or biomolecule of interest.

Binding or stable binding: An association between two substances or molecules, such as the hybridization of one nucleic acid molecule to another or itself, the association of an antibody with a peptide, or the association of a protein with another protein (for example the binding of a transcription factor to a cofactor) or nucleic acid molecule (for example the binding of a transcription factor to a partially double-stranded nucleic acid probe).

Binding can be detected by any procedure known to one skilled in the art, such as by physical or functional properties of the molecular complex. For example, binding can be detected functionally by determining whether binding has an observable effect upon a biosynthetic process such as expression of a gene, DNA replication, transcription, translation, and the like.

Physical methods of detecting the binding of complementary strands of nucleic acid molecules, include but are not limited to, methods such as DNase I or chemical footprinting, gel shift and affinity cleavage assays, Northern blotting, dot blotting and light absorption detection procedures. For example, the method can involve detecting a signal, such as a detectable label, present on one or both nucleic acid molecules (or antibody or protein as appropriate).

The binding between an oligomer and its target nucleic acid can be characterized by the temperature ($T_m$) at which 50% of the oligomer is melted from its target. A higher ($T_m$) means a stronger or more stable complex relative to a complex with a lower ($T_m$).

Biomolecule: A molecule that can be derived from a living organism, such as a polypeptide, a carbohydrate, a lipid, a small molecule and the like. In some examples, with reference to biomolecular polymers, such as polypeptides and nucleic acids, the sequence of polymer need not be found in nature, but can be produced from monomer building blocks, such as nucleotides and amino acids. In addition, the monomers need not be found in nature. A biomolecule can be obtained from organisms live or dead, for example nucleic acids polypeptides, carbohydrates, lipids, small molecules and the like isolated from an organism. Biomolecules also can be artificially produced molecules, such as recombinant polypeptides, nucleic acids, carbohydrates, lipids, small molecules and the like. For example, biomolecules can be produced synthetically or recombinantly. In some examples, a biomolecule is a nucleic acid, such as a RNA, DNA or a combination thereof. In some examples, a biomolecule is a peptide, such as a protein.

Binding site: A region on a protein, nucleic acid (such as DNA, RNA, or a combination thereof) to which other molecules stably bind. In one example, a binding site is the site on a DNA molecule, such as a partially double-stranded nucleic acid probe, that a double-stranded DNA binding protein, such as a transcription factor binds (referred to as a transcription factor binding site).

Buffer solution: An aqueous solution consisting of a mixture of a weak acid and its conjugate base or a weak base and its conjugate acid. It has the property that the pH of the solution changes very little when a small amount of acid or base is added to it. Buffer solutions can keep pH at a nearly constant value in a wide variety of chemical applications.

Complementarity and percentage complementarity: A double-stranded DNA or RNA strand includes of two complementary strands of base pairs (or one strand with a hairpin). Complementary binding occurs when the base of one nucleic acid molecule forms a hydrogen bond to the base of another nucleic acid molecule.

Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide molecule remains detectably bound to a target nucleic acid sequence under the required conditions.

Complementarity is the degree to which bases in one nucleic acid strand base pair with the bases in a second nucleic acid strand. Complementarity is conveniently described by percentage, that is, the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

In the present disclosure, "sufficient complementarity" means that a sufficient number of base pairs exist between an oligonucleotide molecule and a target nucleic acid sequence to achieve detectable binding. When expressed or measured by percentage of base pairs formed, the percentage complementarity that fulfills this goal can range from as little as about 50% complementarity to full (100%) complementary. In general, sufficient complementarity is at least about 50%, for example at least about 75% complementarity, at least about 90% complementarity, at least about 95% complementarity, at least about 98% complementarity, or even at least about 100% complementarity.

A thorough treatment of the qualitative and quantitative considerations involved in establishing binding conditions that allow one skilled in the art to design appropriate oligonucleotides for use under the desired conditions is provided by Beltz et al. *Methods Enzymol.* 100:266-285, 1983, and by Sambrook et al. (ed.), *Molecular Cloning: A Laboratory Manual,* 2nd ed., vol. 1-3, Cold Spring Harbor Laboratory Press, Cold Spring Harbor, NY, 1989.

Contacting: Placement in direct physical association, for example both in solid form and/or in liquid form (for example the placement of a probe in contact with a sample or an electrophoresis gel in contact with a solution, such as an electrophoresis buffer). In some examples, contacting can occur in vitro with isolated cells or substantially cell-free extracts, such as nuclear extracts.

Corresponding: The term "corresponding" is a relative term indicating similarity in position, purpose, or structure. For example, a nucleic acid sequence corresponding to a gene promoter indicates that the nucleic acid sequence is similar to the promoter found in an organism.

Cross-linked polymer: A three-dimensional network formed from the chemical reaction of monomers and a cross-linker.

Double-stranded nucleic acid binding protein: A protein that specifically binds to regions of double-stranded nucleic acids, such as duplex DNA, for example the double-stranded region of a partially double-stranded nucleic acid probe. Transcription factors are particular examples of double-stranded nucleic acid binding proteins, as are sigma factors in prokaryotic organisms.

Emission or emission signal: The light of a particular wavelength generated from a source. In particular examples, an emission signal is emitted from a fluorophore after the fluorophore absorbs light at its excitation wavelengths.

Electromagnetic radiation: A series of electromagnetic waves that are propagated by simultaneous periodic variations of electric and magnetic field intensity, and that includes radio waves, infrared, visible light, ultraviolet light, X-rays and gamma rays. In particular examples, electromagnetic radiation is emitted by a laser, which can possess properties of monochromaticity, directionality, coherence, polarization, and intensity. Lasers are capable of emitting light at a particular wavelength (or across a relatively narrow range of wavelengths), for example such that energy from the laser can excite one fluorophore not another fluorophore.

Electrophoresis: The process of separating a mixture of charged molecules based on the different mobility of these charged molecules in response to an applied electric current. A particular type of electrophoresis is gel electrophoresis. The mobility of a molecule is generally related to the characteristics of the charged molecule, such as size, shape, and surface charge amongst others. The mobility of a molecule also is influenced by the electrophoretic medium, for example the composition of the electrophoresis gel. For example, when the electrophoretic medium is cross-linked acrylamide (polyacrylamide) increasing the percentage if acrylamide in the gel reduces the size of the resulting pores in the gel and retards the mobility of a molecule relative to a gel with a lower percentage of acrylamide (larger pore size). Gel electrophoresis can be performed for analytical purposes, but can be used as a preparative technique to partially purify molecules prior to use of other methods, such as mass spectrometry, PCR, cloning, DNA sequencing, array analysis, and immuno-blotting.

Excitation or excitation signal: The light of a particular wavelength necessary and/or sufficient to excite an electron transition to a higher energy level. In particular examples, an excitation is the light of a particular wavelength necessary and/or sufficient to excite a fluorophore to a state such that the fluorophore will emit a different (such as a longer) wavelength of light then the wavelength of light from the excitation signal.

For a period of time sufficient: A phrase used to describe a period of time in which a desired activity occurs, for example the time it takes for a biomolecule or a complex of biomolecules (molecular complex or biomolecular complex) to pass through a portion of an electrophoresis gel under the influence of an applied electric current. For example, the time it takes for a free biomolecule to travel from a proximal end of a gel to the distal end and elute from the distal end of an electrophoresis gel. In another example, it is the time it takes for a molecular complex, such as a complex containing a biomolecule of interest, to pass from a position within an electrophoresis gel to the end of the electrophoresis gel, and elute from that end. It is appreciated by those of ordinary skill in the art that the period of time sufficient for a free biomolecule to pass from one end of an electrophoresis gel to the other, or the time it takes for a molecular complex, such as a complex containing a biomolecule of interest, to pass from a position within an electrophoresis gel to the end of the electrophoresis gel, and elute the end, will depend on such factors as the composition of the gel, strength of the electric current, and the physical characteristics of the biomolecules or complexes. It is also appreciated that these time periods can be varied by the practitioner according to his or her needs.

Hairpin or nucleic acid hairpin: A nucleic acid structure formed from a single strand of nucleic acid. The strand exhibits self-complementarity, such that the nucleic acid hybridizes with itself, forming a loop at one end.

Hybridization: The ability of complementary single-stranded DNA or RNA to form a duplex molecule (also referred to as a hybridization complex). Nucleic acid hybridization techniques can be used to form hybridization complexes between a probe, such as the single-stranded portion of a partially double-stranded nucleic acid probe and an indexing probe.

Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:
Very High Stringency (Detects Sequences that Share at least 90% Identity)
Hybridization: 5× SSC at 65° C. for 16 hours
Wash twice: 2× SSC at room temperature (RT) for 15 minutes each
sWash twice: 0.5× SSC at 65° C. for 20 minutes each
High Stringency (Detects Sequences that Share at least 80% Identity)
Hybridization: 5×-6× SSC at 65° C.-70° C. for 16-20 hours
Wash twice: 2× SSC at RT for 5-20 minutes each
Wash twice: 1× SSC at 55° C.-70° C. for 30 minutes each
Low Stringency (Detects Sequences that Share at least 50% Identity)
Hybridization: 6× SSC at RT to 55° C. for 16-20 hours
Wash at least twice: 2×-3× SSC at RT to 55° C. for 20-30 minutes each.

Isolated: An "isolated" biological component (such as a protein, a molecular complex, a nucleic acid probe, or free biomolecule) has been substantially separated or purified away from other biological components in the cell of the organism in which the component naturally occurs, for example, extra-chromatin DNA and RNA, proteins and organelles. The term also embraces nucleic acids and proteins prepared by recombinant expression in a host cell as well as chemically synthesized nucleic acids. It is understood that the term "isolated" does not imply that the biological component is free of trace contamination, and can include nucleic acid molecules, proteins or molecular complexes that are at least 50% isolated, such as at least 75%, 80%, 90%, 95%, 98%, 99%, or even 100% isolated.

Label: An agent capable of detection, for example by spectrophotometry, flow cytometry, or microscopy. For example, a label can be attached to a specific binding agent, such as an antibody or a protein, nucleic acid, and the like, thereby permitting detection of the specific binding agent or a biomolecule bound to the specific binding agent. Specific, non-limiting examples of labels include fluorophores, enzymatic linkages, and radioactive isotopes and nanoparticles, such as semiconductor nanocrystals. Methods for labeling are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Molecular complex: Two or more molecules, such as biomolecules, that are stably bound together, for example a nucleic acid binding protein and a nucleic acid molecule, an antibody and an antigen, a ligand and receptor for the ligand, and the like. In some examples, a molecular complex is a transcription factor bound to a nucleic acid that has a binding site for the transcription factor.

Mutation: A change of the DNA sequence relative to the native or wild-type sequence, for example in a promoter of a gene. In some instances, a mutation will alter a characteristic of the DNA sequence, for example the binding of a double-stranded binding protein to the DNA sequence. Mutations include base substitution point mutations, deletions, and insertions as well as combinations thereof. Mutations can be introduced, for example by molecular biological techniques. In some examples, a mutation, such as a mutation in the promoter sequence of a gene, is introduced during synthesis of an oligonucleotide, such as an oligonucleotide that is part of a partially double-stranded nucleic acid probe.

Nucleic acid molecule (or sequence): A deoxyribonucleotide or ribonucleotide polymer including without limitation, cDNA, mRNA, genomic DNA, and synthetic (such as chemically synthesized) DNA or RNA or a combination of DNA and RNA. The nucleic acid molecule can be double stranded (ds) or single stranded (ss) or even partially double-stranded. Where single stranded, the nucleic acid molecule can be the sense strand or the antisense strand. Nucleic acid molecules can include natural nucleotides (such as A, T/U, C, and G), and can also include analogs of natural nucleotides. In one embodiment, a nucleic acid molecule is an aptamer.

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine.

Examples of modified sugar moieties which may be used to modify nucleotides at any position on its structure include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Oligonucleotide or "oligo": Multiple nucleotides (that is, molecules including a sugar (for example, ribose or deoxyribose) linked to a phosphate group and to an exchangeable organic base, which is either a substituted pyrimidine (Py) (for example, cytosine (C), thymine (T) or uracil (U)) or a substituted purine (Pu) (for example, adenine (A) or guanine (G)). The term "oligonucleotide" as used herein refers to both oligoribonucleotides and oligodeoxyribonucleotides. Oligonucleotides can be obtained from existing nucleic acid sources (for example, genomic or cDNA), but are preferably synthetic (that is, produced by oligonucleotide synthesis).

Partially double-stranded nucleic acid probe: A nucleic acid probe that includes both a region that is single-stranded and a region or portion that is double-stranded. A partially double-stranded nucleic acid probe has a portion that is double-stranded and a portion that is single-stranded, wherein the double-stranded and single-stranded portions are connected, for example covalently linked. In some examples, the double-stranded portion includes a binding site for a double-stranded nucleic acid binding protein, such as a transcription factor.

Peptide/Protein/Polypeptide: All of these terms refer to a polymer of amino acids and/or amino acid analogs that are joined by peptide bonds or peptide bond mimetics. The twenty naturally occurring amino acids and their single-letter and three-letter designations are known in the art.

Polymerization: The reaction of monomer molecules together in a chemical reaction to form linear chains or a three-dimensional network of polymer chains. In one embodiment, the polymer polyacrylamide is formed from the polymerization of acrylamide in the presence of a cross-linker, which in some embodiments is N',N-methylenebisacrylamide (BIS). Upon the introduction of catalyst, the polymerization of acrylamide and BIS proceeds via a free-radical mechanism. The most common system of catalytic initiation involves the production of free oxygen radicals by ammonium persulfate (APS) in the presence of the tertiary aliphatic amine N,N,N',N'-tetramethylethylenediamine (TEMED) although other free radical generators can be employed.

Polysaccharide: A polymer of covalently linked sugars. The sugars making up the polysaccharide can by the same sugar or different sugars.

Promoter: An array of nucleic acid control sequences, which directs transcription of a nucleic acid. Typically, a eukaryotic a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription, such as specific DNA sequences that are recognized by proteins known as transcription factors.

In prokaryotes, a promoter is recognized by RNA polymerase and an associated sigma factor, which in turn are brought to the promoter DNA by an activator protein binding to its own DNA sequence nearby.

Reverse: To change direction opposite the initial direction. For example, if a biomolecule is traveling away from position A toward position B, reversing direction would mean that that the biomolecule is traveling away from position B toward position A. Reversing the direction of travel of a biomolecule in an electrophoresis gel can be accomplished by reversing the polarity of an electrophoresis apparatus, for example by reversing the direction of the current, while the gel remains static with respect to the electrophoresis apparatus, or reversing the orientation of the gel with respect to the applied electric current.

Sample: Any quantity of a substance that includes biomolecules (such as nucleic acid and proteins, for example double-stranded nucleic acid binding proteins) that can be used in a method disclosed herein. The sample can be a biological sample or can be extracted from a biological sample derived from humans, animals, plants, fungi, yeast, bacteria, tissue cultures, viral cultures, or combinations thereof.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. One indication that two nucleic acid molecules are closely related is that the two molecules hybridize to each other under stringent conditions. Stringent conditions are sequence-dependent and are different under different environmental parameters.

Target biomolecule or biomolecule of interest: A biomolecule about which information is desired. A target biomolecule or biomolecule of interest can be any molecule that is or once was part of a living organism or synthetically produced. In several non-limiting examples, a target biomolecule is a polypeptide, a nucleic acid, a ligand, or a small molecule. In one example, the information desired is location of the biomolecule on or within a cell, such as a cell in a biological sample. In another example, the information desired is the presence or absence of the biomolecule, for example in a sample, such as a biological sample. In another example, the information desired is the presence, absence, and/or location of the biomolecule in a gel, such as an electrophoreses gel.

Transcription factor: A protein that regulates transcription. In particular, transcription factors regulate the binding of RNA polymerase and the initiation of transcription. A transcription factor binds upstream or downstream to either enhance or repress transcription of a gene by assisting or blocking RNA polymerase binding. The term transcription factor includes both inactive and activated transcription factors.

Transcription factors are typically modular proteins that affect regulation of gene expression. Exemplary transcription factors include AAF, ab1, ADA2, ADA-NF1, AF-1, AFP1, AhR, AIIN3, ALL-1, alpha-CBF, alpha-CP1, alpha-CP2a, alpha-CP2b, alphaHo, alphaH2-alphaH3, Alx-4, aMEF-2, AML1, AML1a, AML1b, AML1c, AML1DeltaN, AML2, AML3, AML3a, AML3b, AMY-1L, A-Myb, ANF, AP-1, AP-2alphaA, AP-2alphaB, AP-2beta, AP-2gamma, AP-3 (1), AP-3 (2), AP-4, AP-5, APC, AR, AREB6, Arnt, Arnt (774 M form), ARP-1, ATBF1-A, ATBF1-B, ATF, ATF-1, ATF-2, ATF-3, ATF-3deltaZIP, ATF-a, ATF-adelta, ATPF1, Barh11, Barh12, Barx1, Barx2, Bc1-3, BCL-6, BD73, beta-catenin, Bin1, B-Myb, BP1, BP2, brahma, BRCA1, Brn-3a, Brn-3b, Brn-4, BTEB, BTEB2, B-TFIID, C/EBPalpha, C/EBPbeta, C/EBPdelta, CACCbinding factor, Cart-1, CBF (4), CBF (5), CBP, CCAAT-binding factor, CCMT-binding factor, CCF, CCG1, CCK-1a, CCK-1b, CD28RC, cdk2, cdk9, Cdx-1, CDX2, Cdx-4, CFF, Chx10, CLIM1, CLIM2, CNBP, CoS, COUP, CP1, CP1A, CP1C, CP2, CPBP, CPE binding protein, CREB, CREB-2, CRE-BP1, CRE-BPa, CREMalpha, CRF, Crx, CSBP-1, CTCF, CTF, CTF-1, CTF-2, CTF-3, CTF-5, CTF-7, CUP, CUTL1, Cx, cyclin A, cyclin T1, cyclin T2, cyclin T2a, cyclin T2b, DAP, DAX1, DB1, DBF4, DBP, DbpA, DbpAv, DbpB, DDB, DDB-1, DDB-2, DEF, delta-CREB, deltaMax, DF-1, DF-2, DF-3, D1x-1, D1x-2, D1x-3, D1x4 (long isoform), D1x-4 (short isoform, D1x-5, D1x-6, DP-1, DP-2, DSIF, DSIF-p14, DSIF-p160, DTF, DUX1, DUX2, DUX3, DUX4, E, E12, E2F, E2F+E4, E2F+p107, E2F-1, E2F-2, E2F-3, E2F-4, E2F-5, E2F-6, E47, E4BP4, E4F, E4F1, E4TF2, EAR2, EBP-80, EC2, EF1, EF-C, EGR1, EGR2, EGR3, EIIaE-A, EIIaE-B, EIIaE-Calpha, EIIaE-Cbeta, EivF, EIf-1, Elk-1, Emx-1, Emx-2, Emx-2, En-1, En-2, ENH-bind. prot., ENKTF-1, EPAS1, epsilonF1, ER, Erg-1, Erg-2, ERR1, ERR2, ETF, Ets-1, Ets-1 deltaVil, Ets-2, Evx-1, F2F, factor 2, Factor name, FBP, f-EBP, FKBP59, FKHL18, FKHRL1P2, Fli-1, Fos, FOXB1, FOXC1, FOXC2, FOXD1, FOXD2, FOXD3, FOXD4, FOXE1, FOXE3, FOXF1, FOXF2, FOXG1a, FOXG1b, FOXG1c, FOXH1, FOXI1, FOXJ1a, FOXJ1b, FOXJ2 (long isoform), FOXJ2 (short isoform), FOXJ3, FOXK1a, FOXK1b, FOXK1c, FOXL1, FOXM1a, FOXM1b, FOXM1c, FOXN1, FOXN2, FOXN3, FOX01a, FOX01b, FOXO2, FOXO3a, FOXO3b, FOXO4, FOXP1, FOXP3, Fra-1, Fra-2, FTF, FTS, G factor, G6 factor, GABP, GABP-alpha, GABP-beta1, GABP-beta2, GADD 153, GAF, gammaCMT, gammaCAC1, gammaCAC2, GATA-1, GATA-2, GATA-3, GATA-4, GATA-5, GATA-6, Gbx-1, Gbx-2, GCF, GCMa, GCN5, GF1, GLI, GLI3, GR alpha, GR beta, GRF-1, Gsc, Gsc1, GT-IC, GT-IIA, GT-IIBalpha, GT-IIBbeta, H1TF1, H1TF2, H2RIIBP, H4TF-1, H4TF-2, HAND1, HAND2, HB9, HDAC1, HDAC2, HDAC3, hDaxx, heat-induced factor, HEB, HEB1-p67, HEB1-p94, HEF-1 B, HEF-1T, HEF-4C, HEN1, HEN2, Hesx1, Hex, HIF-1, HIF-1alpha, HIF-1beta, HiNF-A, HiNF-B, HINF-C, HINF-D, HiNF-D3, HiNF-E, HiNF-P, HIP1, HIV-EP2, H1f, HLTF, HLTF (Met123), HLX, HMBP, HMG I, HMG I(Y), HMG Y, HMGI-C, HNF-1A, HNF-1B, HNF-1C, HNF-3, HNF-3alpha, HNF-3beta, HNF-3gamma, HNF4, HNF-4alpha, HNF4alpha1, HNF-4alpha2, HNF-4alpha3, HNF-4alpha4, HNF4gamma, HNF-6alpha, hnRNP K, HOX11, HOXA1, HOXA10, HOXA10 PL2, HOXA11, HOXA13, HOXA2, HOXA3, HOXA4, HOXA5, HOXA6, HOXA7, HOXA9A, HOXA9B, HOXB-1, HOXB13, HOXB2, HOXB3, HOXB4, HOXB5, HOXB6, HOXA5, HOXB7, HOXB8, HOXB9, HOXC10, HOXC11, HOXC12, HOXC13, HOXC4, HOXC5, HOXC6, HOXC8, HOXC9, HOXD10, HOXD11, HOXD12, HOXD13, HOXD3, HOXD4, HOXD8, HOXD9, Hp55, Hp65, HPX42B, HrpF, HSF, HSF1 (long), HSF1 (short), HSF2, hsp56, Hsp90, IBP-1, ICER-II, ICER-ligamma, ICSBP, Id1, Id1 H', Id2, Id3, Id3/Heir-1, IF1, IgPE-1, IgPE-2, IgPE-3, IkappaB, IkappaB-alpha, IkappaB-beta, IkappaBR, II-1 RF, IL-6 RE-BP, 11-6 RF, INSAF, IPF1, IRF-1, IRF-2, ir1B, IRX2a, Irx-3, 1rx-4, ISGF-1, ISGF-3, ISGF3alpha, ISGF-3gamma, 1s1-1, ITF, ITF-1, ITF-2, JRF, Jun, JunB, JunD, kappay factor, KBP-1, KER1, KER-1, Kox1, KRF-1, Ku autoantigen, KUP, LBP-1, LBP-1a, LBX1, LCR-F1, LEF-1, LEF-1B, LF-A1, LHX1, LHX2, LHX3a, LHX3b, LHX5, LHX6.1a, LHX6.1b, LIT-1, Lmo1, Lmo2, LMX1A, LMX1B, L-My1 (long form), L-My1 (short form), L-My2, LSF, LXRalpha, LyF-1, LyI-1, M factor, Mad1, MASH-1, Max1, Max2, MAZ, MAZ1, MB67, MBF1, MBF2, MBF3, MBP-1 (1), MBP-1 (2), MBP-2, MDBP, MEF-2, MEF-2B, MEF-2C (433 AA form), MEF-2C (465 AA form), MEF-2C (473 M form), MEF-2C/delta32 (441 AA form), MEF-2D00, MEF-2DOB, MEF-2DAO, MEF-2DA'0, MEF-2DAB, MEF-2DA'B, Meis-1, Meis-2a, Meis-2b, Meis-2c, Meis-2d, Meis-2e, Meis3, Meox1, Meox 1a, Meox2, MHox (K-2), Mi, MIF-1, Miz-1, MM-1, MOP3, MR, Msx-1, Msx-2, MTB-Zf, MTF-1, mtTF1, Mxi1, Myb, Myc, Myc 1, Myf-3, Myf-4, Myf-5, Myf-6, MyoD, MZF-1, NC1, NC2, NCX, NELF, NER1, Net, NF III-a, NF NF NF-1, NF-1A, NF-1B, NF-1X, NF-4FA, NF-4FB, NF-4FC, NF-A, NF-AB, NFAT-1, NF-AT3, NF-Atc, NF-Atp, NF-Atx, NfbetaA, NF-CLE0a, NF-CLE0b, NFdeltaE3A, NFdeltaE3B, NFdeltaE3C, NFdeltaE4A, NFdeltaE4B, NFdeltaE4C, Nfe, NF-E, NF-E2, NF-E2 p45, NF-E3, NFE-6, NF-Gma, NF-GMb, NF-IL-2A, NF-IL-2B, NF-jun, NF-kappaB, NF-kappaB(-like), NF-kappaB1, NF-kappaB1, precursor, NF-kappaB2, NF-kappaB2 (p49), NF-kappaB2 precursor, NF-kappaE1, NF-kappaE2, NF-kappaE3, NF-MHCIIA, NF-MHCIIB, NF-muE1, NF-muE2, NF-muE3, NF-S, NF-X, NF-X1, NF-X2, NF-X3, NF-Xc, NF-YA, NF-Zc, NF-Zz, NHP-1, NHP-2, NHP3, NHP4, NKX2-5, NKX2B, NKX2C, NKX2G, NKX3A, NKX3A v1, NKX3A v2, NKX3A v3, NKX3A v4, NKX3B, NKX6A, Nmi, N-Myc, N-Oct-2alpha, N-Oct-2beta, N-Oct-3, N-Oct-4, N-Oct-5a, N-Oct-5b, NP-TCII, NR2E3, NR4A2, Nrf1, Nrf-1, Nrf2, NRF-2beta1, NRF-2gamma1, NRL, NRSF form 1, NRSF form 2, NTF, 02, OCA-B, Oct-1, Oct-2, Oct-2.1, Oct-2B, Oct-2C, Oct-4A, Oct4B, Oct-5, Oct-6, Octa-factor, octamer-binding factor, oct-B2, oct-B3, Otx1, Otx2, OZF, p107, p130, p28 modulator, p300, p38erg, p45, p49erg,-p53, p55, p55erg, p65delta, p67, Pax-1, Pax-2, Pax-3, Pax-3A, Pax-3B, Pax-4, Pax-5, Pax-6, Pax-6/Pd-5a, Pax-7, Pax-8, Pax-8a, Pax-8b, Pax-8c, Pax-8d, Pax-8e, Pax-8f, Pax-9, Pbx-1a, Pbx-1b, Pbx-2, Pbx-3a, Pbx-3b, PC2, PC4, PC5, PEA3, PEBP2alpha, PEBP2beta, Pit-1, PITX1, PITX2, PITX3, PKNOX1, PLZF, PO-B, Pontin52, PPARalpha, PPARbeta, PPARgamma1, PPARgamma2, PPUR, PR, PR A, pRb, PRD1-BF1, PRDI-BFc, Prop-1, PSE1, P-TEFb, PTF, PTFalpha, PTFbeta, PTFdelta, PTFgamma, Pu box binding factor, Pu box binding factor (BJA-B), PU.1, PuF, Pur factor, R1, R2, RAR-alpha1, RAR-beta, RAR-beta2, RAR-gamma, RAR-gamma1, RBP60, RBP-Jkappa, Rel, RelA, RelB, RFX, RFX1, RFX2, RFX3, RFX5, RF-Y, RORalpha1, RORalpha2, RORalpha3, RORbeta, RORgamma, Rox, RPF1, RPGalpha, RREB-1, RSRFC4, RSRFC9, RVF, RXR-alpha, RXR-beta, SAP-1a, SAP1b, SF-1, SHOX2a, SHOX2b, SHOXa, SHOXb, SHP, SIII-p110, SIII-p15, SIII-p18, SIM1, Six-1, Six-2, Six-3, Six-4, Six-5, Six-6, SMAD-1, SMAD-2, SMAD-3, SMAD-4, SMAD-5, SOX-11, SOX-12, Sox-4, Sox-5, SOX-9, Sp1, Sp2, Sp3, Sp4, Sph factor, Spi-B, SPIN, SRCAP, SREBP-1a, SREBP-1b, SREBP-1c, SREBP-2, SRE-ZBP, SRF, SRY, SRP1, Staf-50, STAT1alpha, STAT1beta, STAT2, STAT3, STAT4, STATE, T3R, T3R-alpha1, T3R-alpha2, T3R-beta, TAF(I)110, TAF(I)48, TAF(I)63, TAF(II)100, TAF(II)125, TAF(II)135, TAF(II)170, TAF(II)18, TAF(II)20, TAF(II)250, TAF(II)250Delta, TAF(II)28, TAF(II)30, TAF(II)31, TAF(II) 55, TAF(II)70-alpha, TAF(II)70-beta, TAF(II)70-gamma, TAF-I, TAF-II, TAF-L, Tal-1,Tal-1beta, Tal-2, TAR factor, TBP, TBX1A, TBX1 B, TBX2, TBX4, TBX5 (long isoform), TBX5 (short isoform), TCF, TCF-1, TCF-1A, TCF-1B, TCF-1C, TCF-1D, TCF-1E, TCF-1F, TCF-1G, TCF-2alpha, TCF-3, TCF-4, TCF-4(K), TCF-4B, TCF-4E, TCFbeta1, TEF-1, TEF-2, te1, TFE3, TFEB, TFIIA, TFIIA-alpha/beta precursor, TFIIA-alpha/beta precursor, TFIIA-gamma, TFIIB, TFIID, TFIIE, TFIIE-alpha, TFIIE-beta, TFIIF, TFIIF-alpha, TFIIF-beta, TFIIH, TFIIH*, TFIIH-CAK, TFIIH-cyclin H, TFIIH-ERCC2/CAK, TFIIH-MAT1, TFIIH-MO15, TFIIH-p34, TFIIH-p44, TFIIH-p62, TFIIH-p80, TFIIH-p90, TFII-I, Tf-LF1, Tf-LF2, TGIF, TGIF2, TGT3, THRA1, TIF2, TLE1, TLX3, TMF, TR2, TR2-11, TR2-9, TR3, TR4, TRAP, TREB-1, TREB-2, TREB-3, TREF1, TREF2, TRF (2), TTF-1, TXRE BP, TxREF, UBF, UBP-1, UEF-1, UEF-2, UEF-3, UEF-4, USF1, USF2, USF2b, Vav, Vax-2, VDR, vHNF-1A, vHNF-1B, vHNF-1C, VITF, WSTF, WT1, WT1I, WT1 I-KTS, WT1 I-de12, WT1-KTS, WT1-de12, X2BP, XBP-1, XW-V, XX, YAF2, YB-1, YEBP, YY1, ZEB, ZF1, ZF2, ZFX, ZHX1, ZIC2, ZID, ZNF174, amongst others.

An activated transcription factor is a transcription factor that has been activated by a stimulus resulting in a measurable change in the state of the transcription factor, for example a post-translational modification, such as phosphorylation, methylation, and the like. Activation of a transcription factor can result in a change in the affinity for a particular DNA sequence or of a particular protein, such as another transcription factor and/or cofactor.

Under conditions that permit binding: A phrase used to describe any environment that permits the desired activity, for example conditions under which two or more molecules, such as nucleic acid molecules and/or protein molecules, can bind. Such conditions can include specific concentrations of salts and/or other chemicals that facilitate the binding of molecules. In some examples, conditions that permit binding are similar to the conditions found in the nucleus of a cell, for example a eukaryotic cell or the cytoplasm of a prokaryotic cell. Such conditions can be simulated, for example by using a nuclear extract.

Unitary: Having the indivisible character of a unit. For example, a unitary body can comprise a single body, without removable components.

II. Description of Several Embodiments

A. Devices

FIGS. 1-4 illustrate one embodiment of an electrophoresis cassette body 100 according to the present disclosure. As shown in FIGS. 8-10 and described in further detail below, cassette body 100 can be used in conjunction with one or more buffer baths in order to perform various methods of performing gel electrophoresis.

Returning to FIGS. 1-4, cassette body 100 can include one or more upper chambers 102 adjacent a shelf 106 and one or more lower chambers 104, each in fluid communication with one or more of the upper chambers 102. The terms "upper" and "lower" are used for convenient reference to the figures and are not meant to be limiting in any way.

Each upper chamber 102 and corresponding lower chamber 104 form a respective channel, or through hole, passing from the shelf 106 at the proximal end 108 of the cassette body 100 to the distal end 110. Each upper chamber 102 includes an opening 112 at or near the proximal end 108 of the cassette body 100, and each lower chamber 104 includes an opening 114 at or near the distal end 110 of the cassette body 100. Upper chambers 102 further include a window 116, which results in a portion of upper chamber 102 being open to the space external to cassette body 100. In some embodiments, cassette body 100 can be a monolithic body such that a front face 132 is formed together with, and not removable from, a back face 134. Upper and lower chambers 102, 104 can be defined between the front face 132 and the back face 134.

Upper chambers 102 and lower chambers 104 can be of substantially the same size, shape, and/or capacity, or of different sizes, shapes, and/or capacities. For example, in the embodiments shown in FIGS. 1-3, the lower chambers 104 can be slightly smaller, for example, slightly narrower, than the upper chambers 102.

Embodiments of cassette bodies can be machined, shaped, or molded to engage with one or more other components to form an electrophoresis apparatus. For example, cassette body 100 can be provided with raised lips 118 on edge portions 120, 122. Edge portions 120, 122 can be provided with one or more raised bumps 124 or depressions 126. Some embodiments of cassette bodies can be molded or otherwise formed such that a plurality of cassette bodies can be stacked against or on top of one another. Cassette bodies can be used alone or in conjunction with one or more other cassette bodies in an overall electrophoresis device.

FIG. 5 illustrates a perspective view of a comb 500 that can be used with cassette body 100. As shown in FIG. 6, comb 500 can be shaped to engage with cassette body 100. For example, comb 500 can include a stopper 502, an elongate portion 504, and a projection 506. The stopper 502 can rest within the shelf 106 of the cassette body 100, such that a surface 508 of the comb 500 rests on a surface 510 of the cassette body 100. In this configuration, the elongate portion 504 can be positioned within the upper chamber 102, and the projection 506 can extend into the lower chamber 104. In the embodiment shown in FIG. 6, the volume, or size, of the elongate portion 504 is substantially the same as the volume, or size, of the upper chamber 102. The volume of the projection 506 is substantially smaller than the volume of the lower chamber 104, yet the width of the projection 506 and the lower chamber 104 is substantially the same. Other arrangements, however, are possible. In alternate embodiments, the elongate portion 504 and the projection 506 can be relatively smaller or larger with respect to the upper chamber 102 and lower chamber 104, respectively.

The combs 500 can be sized such that the stoppers 502 substantially fill the volume of the shelf 106 of the cassette body 100. For example, in some embodiments, when the combs 500 are inserted into the upper and lower chambers 102, 104, the stoppers 502 of adjacent combs 500 can be substantially flush, or at least very near, one another, such that edges 512, 514 of neighboring combs contact one another. Comb edges 516, 518 can also be in contact with shelf edges 128, 130, respectively, when the combs 500 are inserted into the upper chambers 102. In alternate embodiments, there can be a space or gap between comb edges 512, 514, and/or between comb edges 516, 518 and shelf edges 128, 130, respectively.

In preparation for running an electrophoresis gel using a cassette according to the present disclosure, such as the cassette body 100 shown in FIGS. 1-4, a compound such as agarose or polyacrylamide can be introduced into the lower chambers 104. One or more combs, such as a comb 500 shown in FIG. 5, can then be positioned within the upper and lower chambers 102, 104, as shown in FIG. 6, such that the projections 506 are positioned within the lower chamber 104, thus displacing a volume of the compound equal to the volume of the projection 504. Once the compound becomes a gel, the combs 500 can be removed from the cassette 100. A cross-linked gel can thus be formed in the lower chambers 104, having an indentation in the upper portion formed by projection 504, adjacent the upper chamber 102, wherein a sample can be loaded.

Cassette bodies according to the present disclosure can be integrated with other components, such as membranes and/or electrodes in order to facilitate providing electrical current to a sample loaded into the chambers of the cassette body.

In some embodiments, as shown in FIG. 7, a membrane 700 can be coupled to a cassette body 702. In some embodiments, a membrane 700 can cover at least a portion of at least one window 704 provided in an upper chamber 706. The membrane 700 also can substantially cover the entire window 704 of each upper chamber 706. Alternatively, a separate membrane 700 can be provided for each window 704. In some embodiments with a plurality of membranes 700, each membrane 700 can be substantially the same thickness, and can comprise the same material. In other embodiments with a plurality of membranes 700, one or more membranes 700 can be different from one or more other membranes 700, such as by being a different thickness and/or comprising a different material.

While membrane 700 is shown to substantially cover the entire front face 708 of the cassette body 702 in FIG. 7, in alternate embodiments, the membrane 700 can cover only a portion of the front face 708 of cassette body 702. For example, in some embodiments, the membrane 700 can be sized such that it extends from the proximal end 716 of the cassette body 702 towards the distal end 718 of the cassette body 702, but does not reach the distal end 718. The membrane 700 can be sized such that it does not extend substantially further than the distal end 720 of the windows 704. The membrane can be configured such that it rests substantially entirely on the front face 708 of the cassette body 702. In alternate embodiments, at least a portion of the membrane 700 can be in contact with and/or secured to one or more of the cassette body sides 710, 712.

One or more membranes 700 can be removably or permanently attached or coupled to any portion of a cassette 702 in any suitable fashion. For example, a membrane 700 can be secured to a cassette body 702 such as by a tape or other adhesive. In other embodiments, one or more membranes 700 can be fixed to a cassette body 702 with screws, clamps, thermal bonding, electrostatic force, or any appropriate method. Membranes 700 can be used to keep the sample physically separate from the electrodes in the buffer pool outside the cassette body, thus substantially avoiding degradation of the biomolecule of interest, which can occur if the sample directly contacts or comes very close to the electrode.

Membranes 700 can comprise any material suitable for the particular application. In some embodiments, membrane 700 can be semi-permeable, allowing a buffer solution to pass through the membrane 700 and into the upper chamber 706, but not allowing other compounds, such as biomolecules of interest, to pass through the membrane 700 into the buffer solution outside of the upper chamber 706. For example, in some embodiments, membrane 700 can comprise a semi-permeable membrane having a molecular weight threshold that allows small molecules to pass through while retaining larger molecules, such as free biomolecules or biomolecules of interest. The molecular weight threshold can be from about 1 kilodalton (kDa) to about 300 kDa or greater. Suitable membrane materials include, by way of example, dialysis filtration material, such as regenerated cellulose, cellophane, or cellulose ester.

In addition to or instead of a membrane, some embodiments of an electrophoresis device according to the present disclosure can include an electrode insert, such as electrode insert 1100, shown in FIGS. 11-12. Electrode insert 1100 can include one or more extensions 1102, 1104, that can position a wire 1106. Screws 1108 can serve as electrode terminals and/or can secure wire 1106 to the electrode insert 1100. The embodiment shown in FIGS. 11-12 includes two extensions 1102, 1104. Other embodiments, however, can include more or fewer than two extensions. In the illustrated embodiment, wire 1106 enters a via 1110 near a first side 1112 of the electrode insert 1100. Via 1110 can allow the wire 1106 to pass from the proximal end 1114 of the electrode insert 1100 to an intermediary surface 1116, and further around a first extension 1102, such that the wire 1106 passes through grooves 1120 provided in the first extension 1102 near the distal end 1118 of the electrode insert 1100. The wire 1106 can then pass through a second via 1122, returning to the proximal end 1114 of the electrode insert, and can continue through a third via 1124, through grooves 1120 of second extension 1104, and finally through a fourth via 1126, thus exiting the electrode insert 1100 at the proximal end 1114, secured with a screw 1108 near the second side 1128 of the electrode insert 1100.

The wire 1106 of electrode insert 1100 can be electrically coupled to a source of electricity (e.g., current), such as a battery or power source. In some embodiments, the wire 1106 can be connected to a positive terminal at one side of the electrode insert 1100, and connected to ground or a negative terminal at the opposite side of the electrode insert 1100. The polarity of such electrical connections can be reversible. Electrode inserts 1100 can be molded or machined of materials such as those described for use with the cassette body. Electrode inserts can be shaped to interconnect or mate with disclosed cassette bodies such that, for example, extensions 1102, 1104 project into the upper chambers of a cassette body, and the intermediary surface 1116 rests on or in the shelf or proximal end of the cassette body.

Wire 1106 can comprise any suitable conductive material. For example, wire 1106 can comprise any metal or metal alloy. In some embodiments, wire 1106 can be coated so as to substantially prevent a buffer solution containing a sample from coming into direct contact with the electrode. For example, the electrode can be coated with platinum, titanium, tantalum, Nafion, and/or combinations thereof.

FIGS. 14-19 illustrate another embodiment of an electrophoresis cassette body 1400 according to the present disclosure. As shown in FIGS. 8-10 and described below, cassette body 1400 can be used in conjunction with one or more buffer baths in order to perform various methods of performing gel electrophoresis. The use of a membrane with the cassette body 1400 can allow for physical separation between the sample and the electrode, thereby preventing degradation of the sample that can result from contact with the electrode.

Cassette body 1400 can include one or more chambers or channels 1402 (best seen in FIGS. 16 and 18) from a proximal opening 1412 at or near a proximal end 1408 of the cassette body 1400 to a distal opening 1414 at or near a distal end 1410 of the cassette body 1400. The chambers 1402 further include a window 1416, which results in an upper portion 1404 of the chamber 1402 being open to the space external to cassette body 1400. For example, the windows 1416 allow for fluid communication between the chambers 1402 and a buffer solution adjacent the front face 1422 of the cassette body.

Opposite the front face 1422, a rear face 1424 can include bored portions 1418 adjacent the distal end 1410 of the cassette body 1400. Such bored portions 1418 can allow for fluid flow around the entire periphery of a lower portion 1432 of the chambers 1402. In some embodiments, the bored portions 1418 can allow for better thermal conditions, such as keeping the contents inside the chambers 1402 cooler than would be the case if fluid flow was not permitted around the entire periphery of the lower portion 1432 of chamber 1402.

Chambers 1402 are shown as substantially cylindrical or tubular chambers 1402, but other configurations are also possible. For example, chambers having substantially oval, square, rectangular, triangular, or other shaped cross-sections are possible.

Figure 14:
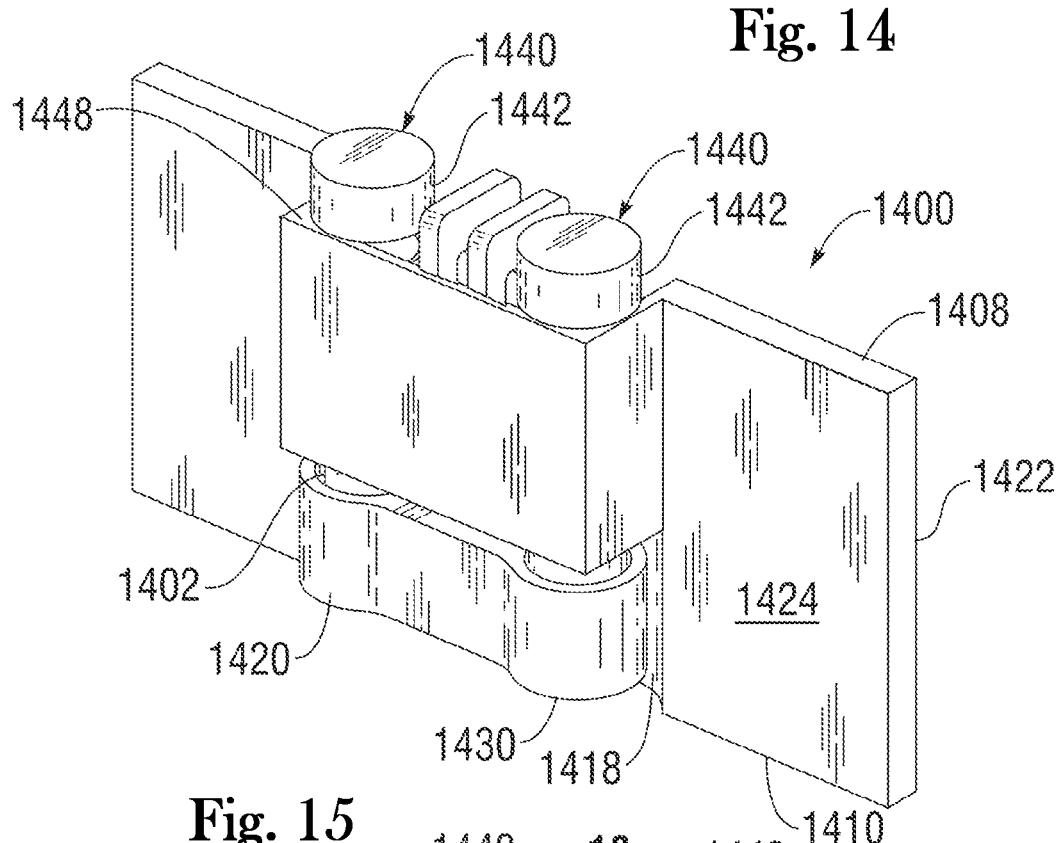
FIG. 14 is a perspective view from the back of another embodiment of an electrophoresis cassette body according to the present disclosure.
Figure 15:
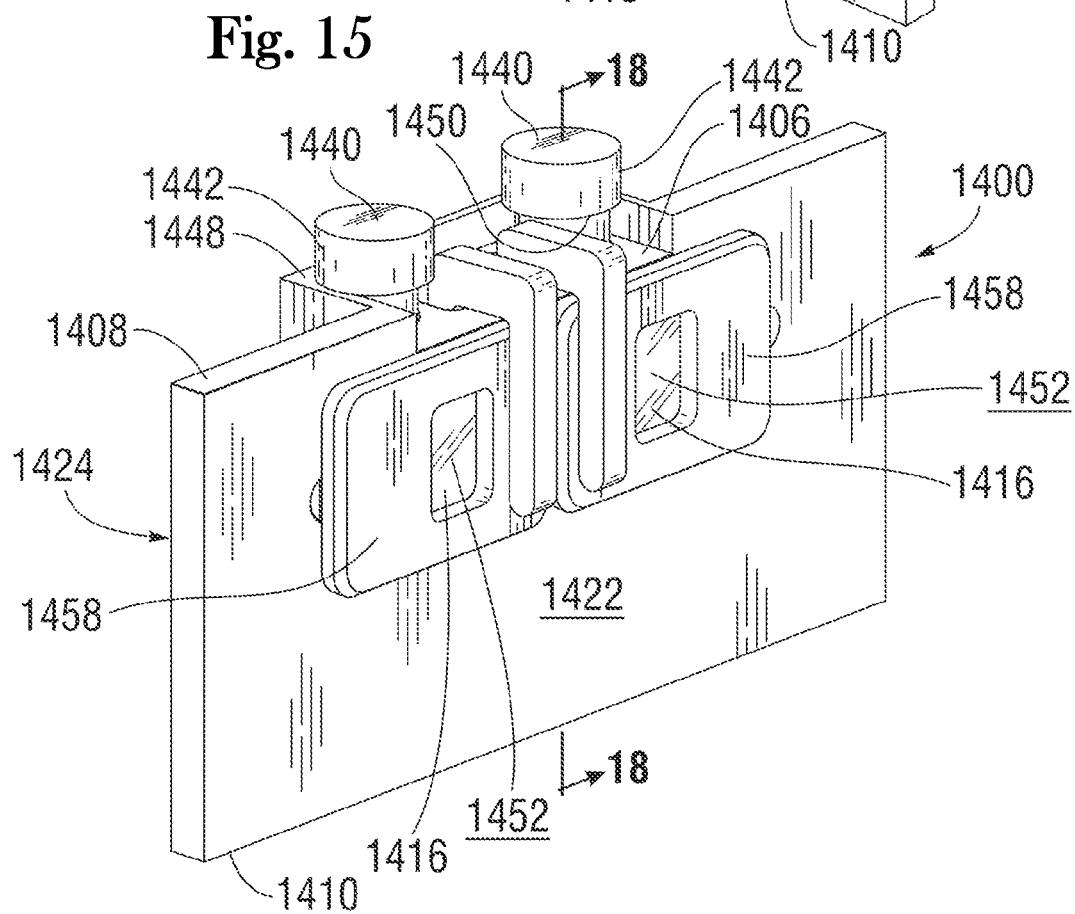
FIG. 15 is a front perspective view of the electrophoresis cassette body of FIG. 14.
Figure 16:
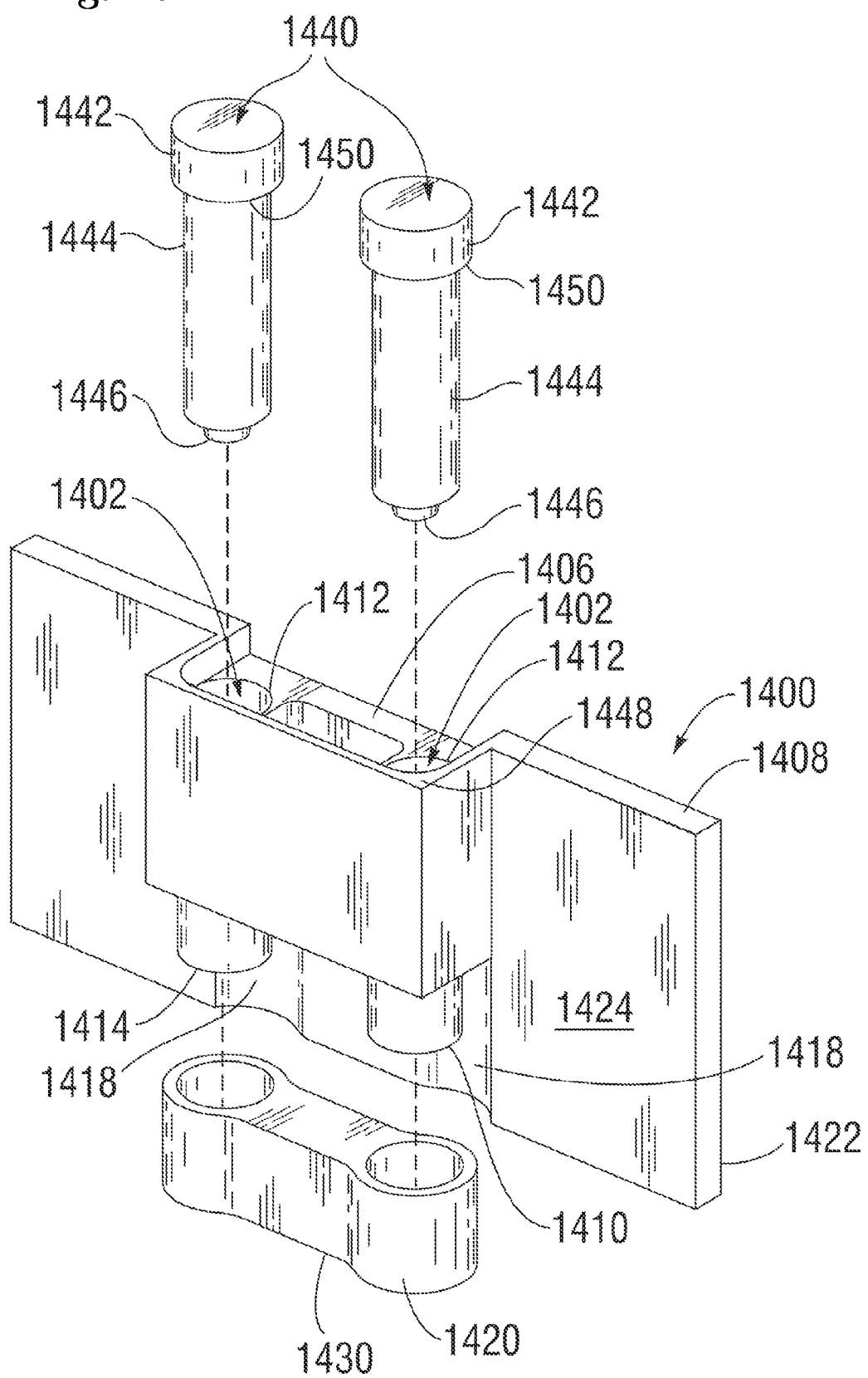
FIG. 16 is a perspective exploded view of the electrophoresis cassette body of FIG. 14.

As best shown in FIGS. 14 and 16, one or more combs 1440 and caps 1420 can optionally be used with cassette body 1400 to form a gel within chamber 1402. Comb 1440 can include a stopper portion 1442, an elongate portion 1444, and a projection 1446. Comb 1440 can be shaped to engage with cassette body 1400. For example, the stopper portion 1442 can be positioned such that at least a portion of surface 1450 of the comb 1440 rests on a recessed surface 1406 and/or a raised surface 1448 of the cassette body 1400. In this configuration, the elongate portion 1444 and the projection 1446 can be positioned within the chamber 1402. In the embodiment shown, the diameter of the elongate portion 1444 is substantially the same as the volume, or size, of the chamber 1402. The volume of the projection 1446 is substantially smaller than the volume of the chamber 1402 and generally can correspond to a sample volume to be electrophoresed in the cassette. Other arrangements are also possible.

Figure 18:
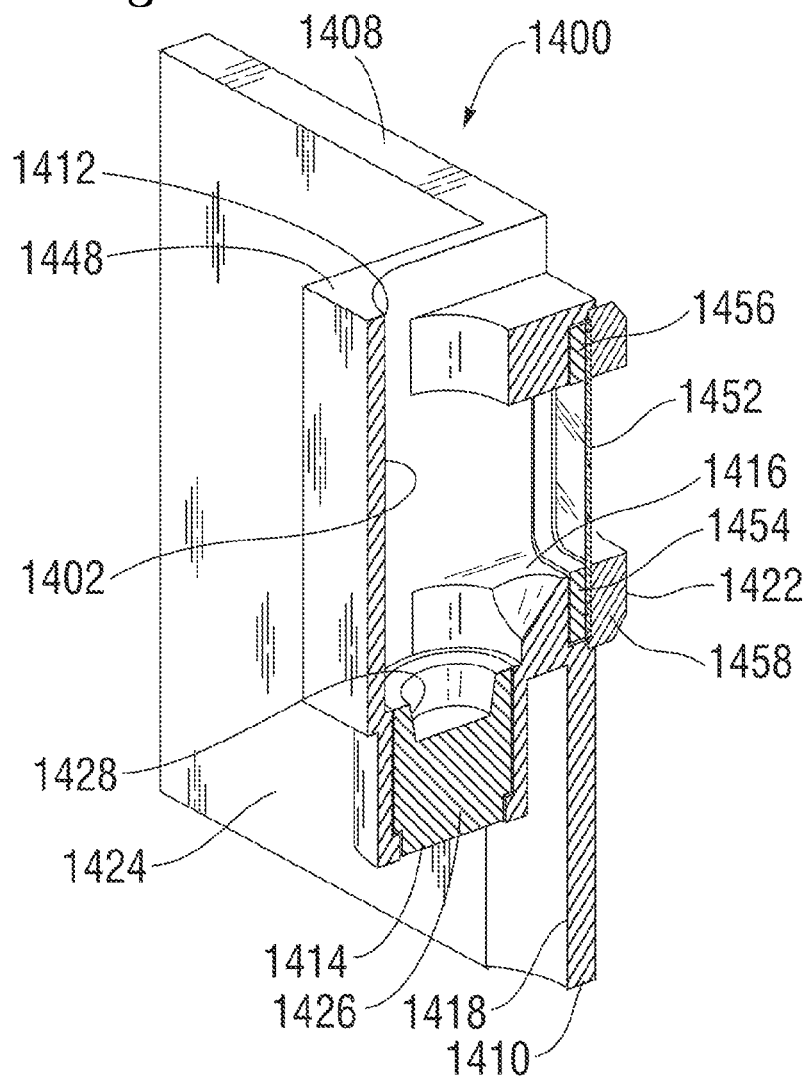
FIG. 18 is a cross-section of the electrophoresis cassette body of FIG. 14, taken along line 18-18 in FIG. 15.
Figure 19:
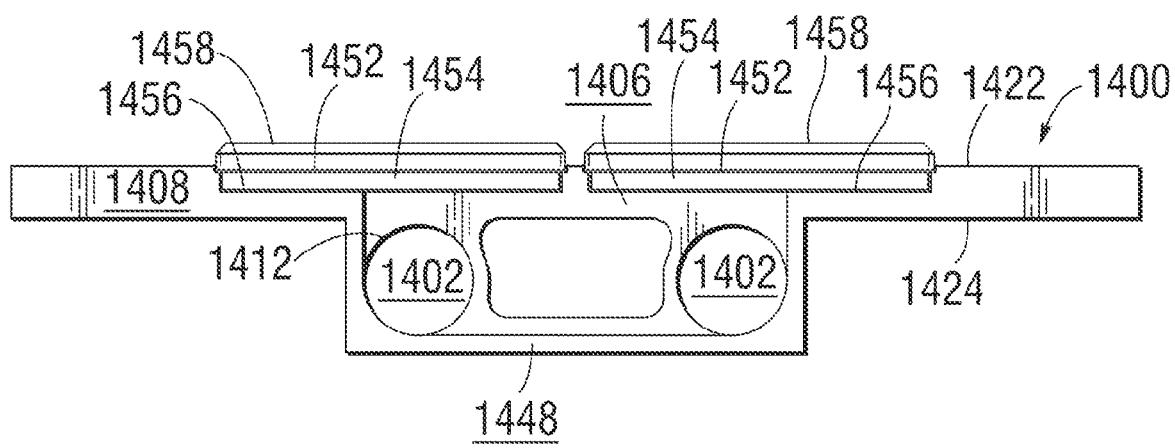
FIG. 19 is a top view of the electrophoresis cassette body of FIG. 14.

A cap 1420 with a seal near the distal end 1430 of the cap 1420 can be positioned such that the cap 1420 closes off the distal openings 1414 of the chambers 1402. In preparation for running an electrophoresis gel using the cassette body 1400, a compound such as agarose or polyacrylamide can be introduced into the chambers 1402. One or more combs 1440 can then be positioned within the chambers 1402 such that the projections 1446 displace a volume of the compound equal to the volume of the projection 1446. Once the compound becomes a gel, the combs 1440 and cap 1420 can be removed from the cassette 1400. As shown in FIG. 18, a cross-linked gel 1426 can thus be formed in the chambers 1402, having an indentation 1428 in the upper portion formed by projection 1446 wherein a sample can be loaded. After removal of the cap 1420, the distal opening 1414 of the chamber 1402 can be in fluid communication with a buffer bath for electrophoresis. Alternatively, a pre-made gel can be inserted into chamber 1402, in which case combs 1440 and caps 1420 would not be used.

Figure 17:
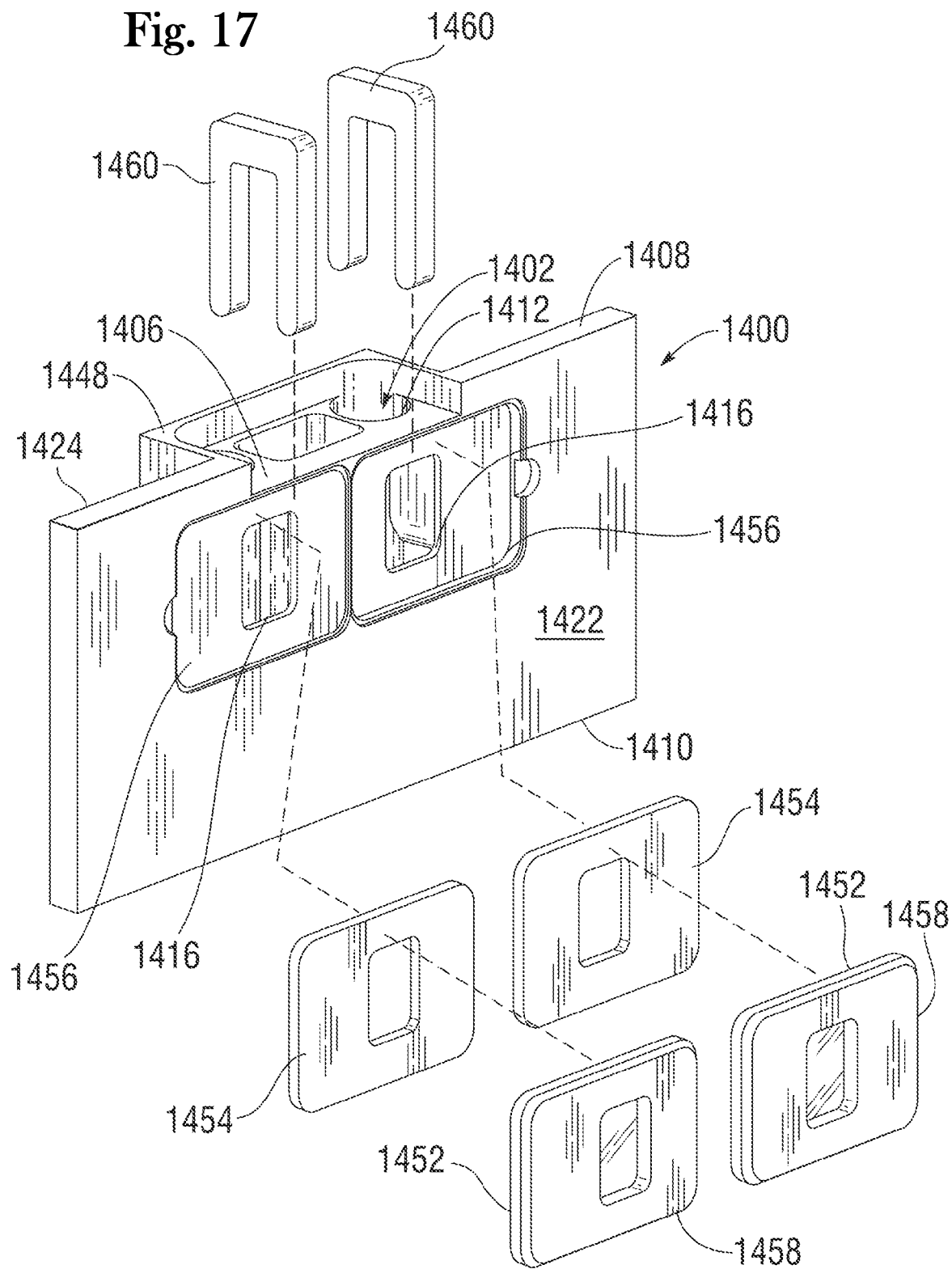
FIG. 17 is a perspective exploded view of the electrophoresis cassette body of FIG. 15.

As best seen in FIGS. 17-18, one or more membranes 1452 can be coupled to the cassette body 1400. Membranes 1452 can be used to keep a sample physically separate from the electrodes in the buffer pool outside the cassette body, thus substantially avoiding degradation of the biomolecule of interest, which can occur if the sample directly contacts or comes very close to the electrode. In some embodiments, one or more membranes 1452 can cover at least a portion of at least one window 1416 provided in a chamber 1402. In other embodiments, one or more membranes 1452 can substantially cover the entire window 1416 of each chamber 1402. Alternatively, as shown in the illustrated embodiment, a separate membrane 1452 can be provided for each window 1416 and desirably is sized to over the entire window. In some embodiments with a plurality of membranes 1452, each membrane 1452 can be substantially the same thickness, and can comprise the same material. In other embodiments with a plurality of membranes 1452, one or more membranes 1452 can be different from one or more other membranes 1452, such as by being a different thickness and/or comprising a different material.

One or more membranes 1452 can be removably or permanently attached or coupled to any portion of a cassette 1400 in any suitable fashion. For example, a membrane 1452 can be secured to a cassette body 1400 such as by tape or other adhesive. In other embodiments, one or more membranes 1452 can be fixed to a cassette body 1400 with screws, clamps, thermal bonding, electrostatic force, or any appropriate method.

A seal 1454, such as a silicone seal, can be positioned adjacent the membrane 1452 so as to prevent leakage around the membrane 1452. For example, in the specific embodiment shown, a recess 1456 can be provided in the front face 1422 of the cassette body 1400 adjacent each window 1416. A membrane 1452 can be positioned in each recess 1456 such that it completely covers the window 1416. A seal 1454 (e.g., a thin silicone rubber seal) can be positioned between the membrane 1452 and the window 1416, as shown in FIGS. 17-18. The seal 1454 can be secured in the cassette body in any suitable fashion. Solely by way of example, in one embodiment the seal 1454 can be retained with a seal cap 1458. The seal cap 1458 can be held in place by welding or bonding it to the cassette body or by using a removable retaining clip 1460 if necessary.

Membranes 1452 can comprise any material suitable for the particular application. In some embodiments, membrane 1452 can be semi-permeable, allowing a buffer solution to pass through the membrane 1452 and into the chamber 1402, but not allowing other compounds, such as biomolecules of interest, to pass through the membrane 1452 into the buffer solution outside of the chamber 1402. For example, in some embodiments, membrane 1452 can comprise a semi-permeable membrane having a molecular weight threshold that allows small molecules to pass through while retaining larger molecules, such as free biomolecules or biomolecules of interest. The molecular weight threshold can be from about 1 kilodalton (kDa) to about 300 kDa or greater. Suitable membrane materials include, by way of example, dialysis filtration material, such as regenerated cellulose, cellophane, or cellulose ester.

Embodiments of cassette bodies can be machined, shaped, or molded to engage with one or more other components to form an electrophoresis apparatus. For example, a cassette body can be provided with fasteners, raised lips, shelves, raised bumps or depressions in order to securely engage a buffer bath. Some embodiments of cassette bodies can be molded or otherwise formed such that a plurality of cassette bodies can be stacked against or on top of one another. Cassette bodies can be used alone or in conjunction with one or more other cassette bodies in an overall electrophoresis device.

While the device shown in FIGS. 1-4 comprises two upper chambers 102 and two lower chambers 104 and the device shown in FIGS. 14-18 comprises two chambers 1402, other embodiments of suitable cassette bodies can contain more or fewer chambers, each of which can receive a separate gel to perform electrophoresis on a separate sample. For example, alternate embodiments of a cassette body can contain only one chamber (or one upper chamber and one lower chamber). Similarly, other embodiments of cassette bodies can contain three or more chambers. Cassette bodies can be configured for vertical and/or horizontal electrophoresis.

Cassette bodies can be constructed from a variety of materials, such as glasses and plastics, such as, for example, acrylic, polycarbonates, polystyrenes, polymethyl methacrylate, polyethylene polyfluoroethylene, polypropylene polyurethane, polyethylene terephthalate, polytetrafluoroethylene and the like. In some embodiments, a cassette body can be molded or machined or otherwise formed from a resin or hard plastic, as appropriate for particular applications. Whereas conventional electrophoresis devices comprises two parallel glass plates, cassette bodies according to the present disclosure can comprise a unitary or monolithic glass or plastic body, for example a machined acrylic body, which can provide advantages such as manufacturing ease and can also allow for easy movement of the cassette body, such as from one buffer bath to another.

Cassette bodies can be combined with an electricity source and one or more buffer baths in order to provide an electrophoresis apparatus. Cassette bodies and electrophoresis apparatus according to the present disclosure can be used in methods of running electrophoresis gels, to, for example, separate and purify a biomolecule of interest.

B. Methods

Embodiments of a method of performing an electrophoresis gel operation are illustrated schematically in FIGS. 8-10 and in a block diagram in FIG. 13. A cassette body 800 (which is a schematic representation of cassette body 100 or cassette body 1440) can comprise an upper chamber portion 802 with a window opening covered by a semi-permeable membrane 804. Semi-permeable membrane 804 can separate the upper chamber portion 802 from a first buffer solution 806 contained in a first container 808. Cassette body 800 can also comprise a lower chamber portion 810, containing a crosslinked native page gel 812 having a sample 814 loaded on top of the gel 812 (e.g., in an indentation at the proximal end of the gel), adjacent the upper chamber portion 802. The gel 812 in the lower chamber portion 810 can be in fluid contact with a second buffer solution 816 contained in a second buffer container 818, such as via a small opening in the bottom of the container 808 adjacent the lower chamber portion 810. The second buffer solution 816 is in fluid contact with the gel 812 but is otherwise separated from the contents of the container 808, including the first buffer solution 806.

An electrical circuit can connect the first buffer solution 806 and the second buffer solution 816 via electrodes 828, 830 (e.g., wires) submerged in the solutions 806, 816. For example, a negative charge can be applied to the first buffer solution 806, and a positive charge can be applied to the second buffer solution 816. Such charges can be applied for a period of time sufficient to separate any free probes 820 in the sample 814 from any biomolecules of interest 822, such as DNA/protein complex 822. For example, charges can be applied for about thirty minutes. During such time, as shown in FIG. 9, free probes 820 can elute out of a distal opening of the lower chamber portion 810 and migrate into the second buffer solution 816, while the DNA/protein complex 822 can remain within gel 812 contained in the lower chamber portion 810 of the cassette body 800.

After the free probes 820 have been separated out, the second buffer solution 816 containing those free probes 820 can be discarded. For example, the second buffer container 818 can be drained of the second buffer solution 816, and a new buffer solution can be added to the second buffer container 818. In alternative embodiments, the cassette body 800 and first buffer container 808 can be removed from their connection with the second buffer container 818, and placed in connection with a new buffer container containing a new buffer solution. In other embodiments, the second buffer solution need not be discarded and can be reused when the current is reversed, as described below.

FIG. 10 illustrates a fresh buffer solution 824, contained in a new buffer container 826. Once the cassette body 800 is arranged such that the first buffer solution 806 is in fluid contact with the semi-permeable membrane 804 and the lower chamber portion 810 is in fluid contact with the fresh buffer solution 824, the polarity of the charges can be reversed. For example, a positive charge can be applied to the first buffer solution, and a negative charge can be applied to the fresh buffer solution 824 for a period of time sufficient for the DNA/protein complex 822 to migrate up from the lower chamber portion 810, out of the gel and into the upper chamber portion 802 (e.g., the DNA protein/complex 822 can migrate towards the proximal end of the cassette body 800). For example, a reverse current can be applied for around forty minutes. A controller 840 (FIG. 8) can be used to automatically control the current polarity. For example, a controller 840 can be programmed to apply a current in one direction for a first predetermined period of time, and then to apply a current in the opposite direction for a second predetermined period of time. Similarly, the controller 840 can be programmed to switch the current polarity at prescribed intervals, as desired by the user. Controller 840 can include, for example, a processor, a display, and one or more control switches for varying parameters.

As shown in FIG. 10, the DNA/protein complex 822 can be contained within some of the buffer solution 806 within the upper chamber 802 of the cassette body 800, substantially without passing through the semi-permeable membrane 804. In some embodiments, buffer solution 806 can pass freely through membrane 804, while the biomolecule of interest 822 substantially cannot pass through the membrane 804. Thus, the DNA/protein complex 822 can be contained within the relatively small volume of the upper chamber portion 802, as opposed to in the large volume of one of the buffer pools. This can allow for easier collection of and simultaneous concentration of a biomolecule of interest, when compared to conventional methods of performing electrophoresis. For example, instead of having to remove a parallel glass plates and slice into the cross-linked gel to gain access to the biomolecule of interest, as is required with typical conventional electrophoresis devices, with embodiments of the present cassette body and electrophoresis device, the biomolecule of interest can simply be contained in a small volume of buffer solution in the upper chamber. This location of the DNA/protein complex 822 can also allow of the cassette body (e.g., easily accessible near the proximal end of the cassette body). In this way, the biomolecule of interest can be collected in a simple way, such as by withdrawing about 500 microliters of solution from the upper chamber of the cassette body via openings along the upper edge of the cassette body, such as by using a micropipette.

Buffer solutions 806, 816, and 824 can be any solution that supports electrophoresis. In some embodiments, solutions 806, 816, and/or 824 can be a salt solution. In some embodiments, solutions 806, 816, and/or 824 can be a buffer solution. Examples of salt solutions include: NaCl, KCl and the like. Examples of buffer solutions include: Tris, HEPES, MOPS, PBS, EDTA, Tris Buffered Saline, Tris-Borate-EDTA (TBE), TAE, TGE, glycerol, glycine and the like, and mixtures thereof. In certain embodiments, the first buffer solution 806 (referred to as the collection buffer solution) comprises glycerol, Tris, glycine and EDTA. In a specific implementation, the first buffer solution 806 comprises 5% glycerol (by volume), 0.75M Tris pH 8.4, 38 mM glycine, and 2 mM EDTA.

While the embodiments shown in FIGS. 8-10 show a cassette body having a membrane covering an opening to the upper chamber portion, other embodiments can comprise an electrode insert that submerges at least a portion of a wire into the upper chamber of the cassette body, in addition to or instead of membrane 804. Exemplary electrode inserts are described above.

FIG. 13 illustrates a block diagram of one method of performing an electrophoresis operation using the electrophoresis devices and cassette bodies according to the present disclosure. The methods can include, loading a sample that includes the free biomolecules and the complexes that include the biomolecules of interest (which can include a detectable label) to the proximal end of the electrophoresis gel, for example in a cassette body arranged in buffer solutions, as described above (step 1300). The sample can be electrophoresed for a period of time sufficient for the free biomolecules to elute from the distal end of the electrophoresis gel, such that the period of time is not long enough so that the complexes including the biomolecules of interest elute from the distal end of electrophoresis gel and are therefore retained in the electrophoresis gel (step 1302). In this way, the complexes including the biomolecules of interest can be separated from the free biomolecules. The time required for the free biomolecules to pass through the gel is dependent upon such factors as applied current, buffer conditions, gel concentration and gel length and the physical characteristics of the biomolecules. The free biomolecules can be discarded, for example by letting them elute from the distal end of the gel into surrounding buffer, or they can be collected, for example using a collector attached to the end of the gel, such as a collector with a semi-permeable membrane that allows buffer through, but retains the free biomolecules (step 1304).

Once the buffer solution containing the free biomolecules has been removed, a clean buffer solution can be provided (step 1306) to replace the buffer solution containing the free biomolecules. Removing the buffer solution contaminated with free biomolecules can substantially prevent the free biomolecules from migrating back up into the gel and upper chamber of the cassette when the current is reversed. Thus, an isolated biomolecule of interest can be collected. However, in alternative embodiments, the buffer solution need not be discarded or replaced. To collect the complexes containing the biomolecules of interest, the current can be reversed relative to the electrophoresis gel, and the biomolecules remaining in the gel can reverse their direction of travel relative to the electrophoresis gel (step 1308).

Reversing the current relative to the electrophoresis gel can be done by reversing the polarity of an electrophoresis apparatus, for example by reversing the direction of the current, while the gel is kept in the same position with respect to the electrophoresis apparatus. In alternative embodiments, the orientation of the gel can be reversed with respect to the applied electric current, without reversing the direction of the current. The gel can then electrophoresed for a second period of time sufficient for the complexes of bound biomolecules of interest to elute from the proximal end of the electrophoresis gel (step 1310). The biomolecules of interest can then be collected, for example using a collector attached to the end of the gel, such as a collector with a semi-permeable membrane that allows buffer through, but retains the biomolecules of interest (step 1312). In some embodiments, the collector can be an integral part of the cassette, as described above, or a separate component mounted on the gel. In some embodiments, the biomolecules of interest can be collected, such as with a micropipette, from the upper chamber of the cassette body.

Any biomolecule of interest can be purified using the disclosed methods. For example the methods disclosed herein can be used to purify nucleic acids of interest or polypeptides of interest. Thus, in some examples a biomolecule of interest is a polypeptide, such as a peptide or protein, for example a receptor, a receptor ligand, an antibody, an antigen, a soluble protein, or an insoluble protein and the like. In some examples polypeptides of interest include one or more antibodies. In some embodiments, polypeptides of interest include one or more antigens. In some examples, the biomolecules of interest are nucleic acid molecules, such as DNA, RNA or combinations thereof.

In some embodiments, the biomolecule of interest is a nucleic acid that is double stranded, single stranded, or a combination thereof. In some embodiments, the biomolecules of interest are partially double-stranded nucleic acid probes, such as those described in International Patent Publication WO 2008/147899, which is incorporated herein by reference in its entirety. International Patent Publication WO 2008/147899 claims the benefit of U.S. Provisional Application No. 60/939,826 which is also incorporated herein by reference in its entirety. Further details, including suitable gel materials, suitable membrane materials, and suitable buffer solution materials can be found in PCT Application PCT/US09/35689, which is hereby incorporated herein by reference in its entirety.

An application of the disclosed methods is the rapid and efficient determination of the sequence binding requirements for a given double-stranded nucleic acid binding protein, such as a double-stranded DNA binding protein, for example a transcription factor, such as an activated transcription factor. For example, by constructing a library of different double-stranded sequences and determining which sequences a particular transcription factor binds to it, it is possible to rapidly identify the sequence requirements for a given transcription factor in a high throughput manner. Using the disclosed methods, such double-stranded sequences bound by transcription factors can be rapidly purified from unbound double-stranded sequences.

In some examples, a partially double-stranded nucleic acid probe includes two portions, a double-stranded portion and a single-stranded portion. The single-stranded portion includes a nucleotide sequence corresponding to an index sequence, such as but not limited to the index sequences described in International Patent Publication WO 2008/147899, which is incorporated herein by reference in its entirety. International Patent Publication WO 2008/147899 claims the benefit of U.S. Provisional Application No. 60/939,826, which is also incorporated herein by reference in its entirety.

The second portion of a partially double-stranded nucleic acid probe is a double-stranded portion selected such that it contains one or more potential binding sites for double-stranded nucleic acid binding proteins, such as transcription factors. For example, a partially double-stranded nucleic acid probe can contain 1, 2, 3, 4, 5, 6, 7, 8, 9, 10, or even more potential binding sites for double-stranded nucleic acid binding proteins, such as transcription factors, for example activated transcription factors. The double-stranded portion of the disclosed partially double-stranded nucleic acid probes are typically greater than about 8 nucleotide base pairs in length such as greater than about 8, about 9, about 10, about 11, about 12, about 13, about 14, about 15, about 20, about 25, about 30, about 35, about 40, about 45, about 50, about 60, about 70, about 80, about 90, about 100, about 120, about 140, about 160, about 180, about 200, about 250, about 300, or even greater than about 350 base pairs in length such as 8-50 nucleotides, 8-100 nucleotides, 8-200 nucleotides, 8-300 nucleotides, 8-500 nucleotides, or even greater than 500 nucleotides in length.

For the detection and/or isolation of biomolecules of interest, biomolecules of interest can include a label. The binding partner(s) of biomolecules of interest can include a label. Thus, in some embodiments, the biomolecules of interest and/or their binding partners are detectably labeled, with any isotopic or non-isotopic label known in the art. Non-isotopic labels can, for instance, include a fluorescent or luminescent molecule, biotin, an enzyme or enzyme substrate or a chemical. Isotopic labels can, for instance, include $^{35}S$ $^{14}C$, $^{32}P$, $^{125}I$, $^{3}H$ isotopes and the like. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

The methods described above are depicted schematically in FIGS. 8-10. Again with reference to FIG. 8, a sample 814 is applied to a proximal end 832 of the electrophoresis gel 812. With reference to FIG. 9, as current is applied by the application of an electric field to electrophoresis gel 812, the biological macromolecules (such as the free biomolecules and complexes containing biomolecules of interest) are separated by the distance traveled through the gel as a function of time (the direction of migration is indicated by arrow 836). Still with reference to FIG. 9, (in which the free biomolecules have a lower molecular weight) the free biomolecules will travel further as a function of time compared to molecular complexes that contain a biomolecule of interest because the molecular complexes have larger molecular weights.

The sample 814 that included the free biomolecules 820 and molecular complexes 822 is electrophoresed for a period of time sufficient for the free biomolecules 820 to elute off distal end 834 of electrophoresis gel 812 into the buffer solution 816. The period of time is not long enough so that the complexes including the biomolecules of interest 822 elute from distal end 834 of electrophoresis gel 812, but rather the biomolecules of interest 822 are retained in electrophoresis gel 812. The free biomolecules 820 can be discarded, for example by letting them flow into the surrounding buffer 816, or they can be collected, for example using a collector, which can contain a semi-permeable membrane with a molecular weight threshold that allows the buffer to pass through but retains the free biomolecule 820 (exemplary semi-permeable membranes are described above).

With reference to FIG. 10, the direction of electrophoresis is subsequently reversed, for example by reversing the polarity of electrodes 828, 830. The biomolecules of interest 822 then travel in a direction opposite to the direction in which they originally traveled (as indicated by arrow 838). Electrophoresis is continued for a period of time sufficient for the complexes of bound biomolecules of interest 822 to elute from proximal end 832 of the electrophoresis gel 812. The molecular complexes of bound biomolecules of interest 822 can be collected, for example using a collector, which can contain semi-permeable membrane with a molecular weight threshold that allows the buffer 806 to pass through but retains the molecular complexes 822 (exemplary semi-permeable membranes are described above). In other embodiments, the biomolecules of interest can be collected from the upper chamber 802, such as with a micropipette.

Biomolecules of interest and isolated molecular complexes can be collected and used for any purpose, for example for further analysis. In some examples, the biomolecules of interest are nucleic acid molecules, for example nucleic acid molecules to which transcription factors have bound. Thus, the methods can be used to separate nucleic acid molecules to which transcription factors have bound from nucleic acid molecules that have not been bound by transcription factors. The complexes containing such transcription factors can be collected and analyzed, for example using the methods described in International Patent Publication WO 2008/147899, which is incorporated herein by reference in its entirety. International Patent Publication WO 2008/147899 claims the benefit of U.S. Provisional Application No. 60/939,826 which is also incorporated herein by reference in its entirety. In other examples, the methods disclosed herein are used to separate protein complexes from free protein, for example a complex of antigen and antibody from free antigen or conversely from free antibody.

Cassette bodies according to the present disclosure can thus be used in methods of performing electrophoresis to separate and/or purify biomolecules of interest from a sample, while avoiding contact between the electrode and the sample, thus substantially avoiding the risk of damaging or denaturing the biomolecule of interest.

C. Electrophoresis Gels

The methods and devices disclosed herein involve the use of an electrophoresis gel for the separation and/or purification of biomolecules of interest, such as biomolecules of interest in a molecular complex. Electrophoresis gels suitable for the disclosed methods include gels composed of one or more polysaccharides (such as agarose), crossed linked polymers (a combination of cross-linkable monomers, for example acrylamide, that can be polymerized by a cross-linker, for example N,N'-methylenebisacrylamide) and combinations thereof.

The electrophoresis gels for use in the disclosed methods can be made from at least one polysaccharide, such as at least 1, at least 2, at least 3, at least 4, or more polysaccharides. In some embodiments, the polysaccharide is agarose or an agarose derivative, such as an agarose derivative which contains hydroxyethyl groups (for example, those disclosed in U.S.

Pat. Nos. 3,956,273 and 4,319,975, or available from a commercial source, such as SEAKEM®, or NUSIEVE®), and the like. In other embodiments, the polysaccharide is cellulose or a cellulose derivative, such as hydroxyethyl cellulose, hydroxypropylmethyl, cellulose methyl cellulose, or the like. Agarose and cellulose are similar in that they are both linear polymers. They differ in their sugar constituents, in glycosidic linkages, and in the ability to form gels. While derivatized celluloses remain in solution at high and low temperatures, agarose polymers form thermally reversible gels. In other embodiments, the polysaccharide is galactomannan, dextran, starch, levan, glucan, mannan, xylan, or other polysaccharide. In specific embodiments, the polysaccharide is agarose, a derivative thereof, or a combination thereof.

Electrophoresis gels useful for the disclosed methods typically contain from about 0.1% polysaccharide to about 7% polysaccharide, such as about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0% about 5.1%, about 5.2%, about 5.3%, about 5.4%, about 5.5%, about 5.6%, about 5.7%, about 5.8%, about 5.9%, about 6.0% about 6.1%, about 6.2%, about 6.3%, about 6.5%, about 6.5%, about 6.6%, about 6.7%, about 6.8%, about 6.9%, or about 7.0% polysaccharide. The choice of percentage can be made based on factors such as the resolution required and the polysaccharide selected.

The electrophoresis gels made from cross-linked polymers for use in the disclosed methods can include the reaction mixture from the free radical polymerization reaction product of a mixture of at least one monomer, such as at least 1, at least 2, at least 3, at least 4, or more monomers, and at least one cross-linker, such as at least 1, at least 2, at least 3, at least 4 or more cross-linkers sufficient to cross-link the monomer. Suitable cross-linkable monomers include acrylamide, acrylamide derivatives (such as N-methylacrylamide, N,N-dimethylacrylamide, N-(hydroxymethyl)acrylamide, diacetonacrylamide, N-hydroxypropylacrylamide, and those disclosed in U.S. Pat. No. 5,185,466), other monomers, such as those disclosed in U.S. Pat. No. 5,840,877 (for example N-acryloyl-tris(hydroxymethyl)aminomethane, or N-acryloyl-1-amino-1-deoxy-D-galactitol), or a combination thereof. Other monomers that can be used in the disclosed methods include the acrylic monomers based on sugar alcohols disclosed in U.S. Pat. Nos. 5,185,466 and 5,202,007 and those disclosed in U.S. Pat. No. 5,319,046. It is contemplated that any of the monomers described herein can be used in the disclosed methods in any combination such that the resultant polymer gel is capable of separating biomolecules. In some embodiments, the monomer is acrylamide, N-methylacrylamide, N,N-dimethylacrylamide, N-(hydroxymethyl)acrylamide, diacetonacrylamide, N-hydroxypropylacrylamide, N-acryloyl-tris(hydroxymethyl)aminomethane, N-acryloyl-1-amino-1-deoxy-D-galactitol, or a combination thereof. In specific embodiments, the monomer is acrylamide. A cross-linking agent, such those described in Gelfi and Righetti *Electrophoresis* 2:213-219, 1981, or known to those of skill in the art can be used to form the crosslinked polymer gels for use in the disclosed methods. Crosslinked polymer gels suitable for the disclosed methods contain a cross-linker capable of cross-linking the monomers described herein. In some embodiments, the cross-linker is N,N'-methylenebisacrylamide, N,N'-propylenebisacrylamide, diacrylamide dimethylether, 1,2-diacrylamide ethyleneglycol, ethylenureabisacrylamide, ethylene diacrylate, N,N'-diallyltartardiamide, N,N'-bisacrylylcystamine, N,N'-1,2-dihydroxyethylenebisacrylamide, N,N-bisacrylyl cystamine, trisacryloylhexahydrotriazine, dihydroxyethylene-bis-acrylamide, piperazine-di-acrylamide, or a combination thereof. In certain embodiments, the cross-linker is N,N'-methylenebisacrylamide (BIS). Cross linking agents are typically used in an amount of about 2% to about 30% by weight and preferably about 3% to about 15% by weight, based on the total weight of the monomer (such as acrylamide) and the cross-linking agent. Higher percentages of cross-linker typically result in gels that increase in opacity as the percentage of cross-linker increases.

In some examples, cross-linked polymer electrophoresis gels useful for the disclosed methods contain from about 0.1% cross-linked monomer to about 15% cross-linked monomer, such as about 0.1%, about 0.5%, about 1.0%, about 1.5%, about 2.0%, about 2.5%, about 3.0%, 3.5%, about 4.0%, about 4.5%, about 5.0%, about 6.0%, about 7.0%, about 7.5%, about 8.0%, about 8.5%, about 9.0%, about 9.5%, about 10.0%, 10.5%, about 11.0%, about 11.5%, about 12.0%, about 12.5%, about 13.0%, 13.5%, about 14.0%, about 14.5%, or about 15.0 cross-linked monomer. The choice of percentage can be made based on factors such as the resolution required and the monomer selected. For example, a percentage of monomer is chosen that is capable if resolving a biomolecule of interest from free biomolecules.

The cross-linking polymerization can be initiated in the presence of a peroxide and/or under irradiation of ultra-violet rays. The reaction can be further accelerated by heat and irradiation with ultra-violet rays. As the polymerization catalyst, a known low temperature-polymerization initiator can be used, such as those described in Gelfi and Righetti *Electrophoresis* 2:213-219, 1981, Gelfi and Righetti *Electrophoresis* 2:220-228, 1981; and *Modern Electrophoresis* edited by Aoki and Nagai (Hirokawa Shoten, 1973). Examples of initiators include a mixture of beta-dimethylaminopropionitrile and ammonium peroxodisulfate, a mixture of N,N,N',N'-tetramethylethylenediamine (TEMED) and ammonium peroxodisulfate, a mixture of TEMED and riboflavin, a combination of a mixture of TEMED, riboflavin and hydrogen peroxide, and irradiation with ultra-violet rays. The most common system of catalytic initiation involves the production of free oxygen radicals by ammonium persulfate (APS) in the presence of the tertiary aliphatic amine TEMED.

The gel-based electrophoretic embodiments of this disclosure can be carried out in any suitable format, for example in standard-sized gels, tubes, minigels, strips, capillaries, and gels designed for use with microtiter plates and other high throughput (HTS) applications, and the like. Formats for gels include those described in U.S. Pat. Nos. 5,578,180; 5,922,185; 6,057,106; 6,059,948; 6,096,182; 6,143,154; 6,162,338; 6,562,213, U.S. Patent Publications 20020134680, 20030127330 and 20030121784; and published PCT Application Nos. WO 95/27197, WO 99/37813, WO 02/18901 and WO 02/071024.

D. Samples

Appropriate samples for use in the methods disclosed herein include any conventional biological sample for which separation and/or purification of biomolecules of interest is desired. In some examples, samples can be samples of purified biomolecules, for example biomolecules recombinantly or synthetically produced or purified from a biological source such as an organism. In some examples, samples include those obtained from, excreted by or secreted by any living organism (whether the organism is live or dead), such as a prokaryotic organism or a eukaryotic organism including without limitation, multicellular organisms (such as plants and animals, including samples from a healthy or apparently healthy human subject or a human patient affected by a condition or disease to be diagnosed or investigated, such as cancer), clinical samples obtained from a human or veterinary subject, for instance blood or blood-fractions, biopsied tissue. Standard techniques for acquisition of such samples are available. See, for example Schluger et al., *J. Exp. Med.* 176:1327-33 (1992); Bigby et al., *Am. Rev. Respir. Dis.* 133:515-18 (1986); Kovacs et al., *NEJM* 318:589-93 (1988); and Ognibene et al., *Am. Rev. Respir. Dis.* 129:929-32 (1984).

Biological samples can be obtained from any organ or tissue (including a biopsy or autopsy specimen, such as a tumor biopsy) or can comprise a cell (whether a primary cell or cultured cell) or medium conditioned by any cell, tissue or organ. In some embodiments, a biological sample is a nuclear extract. Nuclear extract contains many of the proteins contained in the nucleus of a cell, and includes for example transcription factors, such as activated transcription factors. Methods for obtaining a nuclear extract are well known in the art and can be found for example in Dignam, *Nucleic Acids Res*, 11;11(5):1475-89 1983.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A cassette for use with an electrophoresis device, comprising:
   a proximal end and a distal end opposite the proximal end;
   a front face and a back face;
   at least one chamber defined between the front face and the back face, the chamber having an upper portion and a lower portion, wherein the upper portion includes a proximal opening at or near the proximal end of the cassette and the lower portion includes a distal opening at or near the distal end of the cassette; and
   a removable comb positioned within the upper portion of the chamber and extending into the lower portion of the chamber;
   and wherein the front face comprises at least one window opening into the upper portion of the chamber; and a semi-permeable membrane covering at least a portion of the at least one window opening.

2. The cassette according to claim 1, wherein the semi-permeable membrane is removably secured to the front face of the cassette.

3. The cassette according to claim 2, wherein the semi-permeable membrane is configured to allow buffer solution outside the cassette to pass through the membrane into the upper portion of the chamber, and to block passage of a biomolecule contained within the upper portion of the at least one chamber.

4. The cassette according to claim 1, wherein the cassette comprises glass.

5. The cassette according to claim 1, wherein the cassette comprises a unitary body.

6. The cassette according to claim 1, wherein the inner surface of the chamber is substantially cylindrical.

7. The cassette according to claim 1, further comprising a bored portion formed in the back face, wherein the bored portion is configured to allow fluid flow around the entire periphery of at least a portion of the lower portion of the chamber.

8. The cassette according to claim 1, further comprising an electrophoresis gel.

9. The cassette according to claim 8, wherein the gel is a polyacrylamide gel.

* * * * *